US006245902B1

(12) United States Patent
Linhardt et al.

(10) Patent No.: US 6,245,902 B1
(45) Date of Patent: Jun. 12, 2001

(54) C-GLYCOSIDE ANALOGS AND METHODS FOR THEIR PREPARATION AND USE

(75) Inventors: Robert J. Linhardt, Iowa City; Helene G. Bazin, Muscatine, both of IA (US); Yuguo Du, Beijing (CH); Tulay Polat, Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 0 days.

(21) Appl. No.: 09/370,493

(22) Filed: Aug. 9, 1999

(51) Int. Cl.[7] .......................... C07H 15/04; C07H 15/10; C07H 1/00
(52) U.S. Cl. ..................... 536/4.1; 536/1.11; 536/17.9; 536/18.5; 536/119; 536/123; 536/123.13
(58) Field of Search .................................... 536/1.11, 4.1, 536/18.5, 119, 123, 123.13, 17.9

(56) References Cited

U.S. PATENT DOCUMENTS

| | | | |
|---|---|---|---|
| 5,143,712 | * | 9/1992 | Brandley et al. ...................... 424/1.1 |
| 5,211,936 | * | 5/1993 | Brandley et al. ...................... 424/1.1 |
| 5,211,937 | * | 5/1993 | Brandley et al. ...................... 424/1.1 |
| 5,648,344 | * | 7/1997 | Brandley et al. ....................... 514/61 |
| 5,658,880 | * | 8/1997 | Dasgupta et al. ......................... 514/8 |

FOREIGN PATENT DOCUMENTS

98/31696 * 7/1998 (WO).

OTHER PUBLICATIONS

Svennerholm, Lars. "Designation and Schematic Structure of Gangliosides and Allied Glycosphingolipids", Biological Function of Gangliosides, vol. 101, pp. XI–XIV, 17 and 78, 1994.*
Dictionary of Microbiology and Molecular Biology, published by John Wiley & Sons, p. 827, 1996.*
Vlahov et al. "Diastereocontrolled Synthesis of Carbon Glycosides of N–Acetylneuraminic Acid via Glycosyl Samarium (III) Intermediates", J. Amer. Chem. Soc., 119: 1480–1481, 1997.*
Bazin et al. "Synthesis of a Versatile Neuraminic Acid "C"–Disaccharide Precursor for the Synthesis of C–Glycoside Analogues of Gangliosides", J. Org. Chem., 64: 7254–7259, Sep. 1999.*
"Gangliosides", The Merck Index, Tenth Edition, Martha Windholz Editor, 4227 p. 623, (1983).
Air, G.M., et al., "The Neuraminidase of Influenza Virus", Proteins: Structure, Function and Genetics, 6(4), 341–356, (1989).
Bremer, E., et al., "Ganglioside–mediated Modulation of Cell Growth", Journal of Biological Chemistry, 261(5), 2434–2440, (1986).
Carubia, J.M., et al., "Gangliosides of Normal and Neoplastic Human Melanocytes", Biochemical Biophysical Research Communications, 120(30), 500–504, (1984).

Du, Y., et al., "Stereospecific Synthesis of α–C–Glycosyl Derivatives ("α–C–Glycosides") of N–Acetylneuraminic Acid by Samarium–mediated Reductive Desulfonylation of a Glycosyl Phenylsulfone", Carbohydrate Research, 308, 161–164, (1998).
Du, Y., et al., "The Stereospecific Synthesis of KDN α–C–Glycosides by Samarium Mediated Reductive Desulfonylation of Glycosyl Phenylsulfone", Tetrahedron Letters, 39, 5007–5010, (1998).
Hakamori, S., "Glycosphingolipids in Cellular Interaction, Differentiation, and Oncogenesis", Annual Review of Biochemistry, 50, 733–764, (1981).
Hanai, N., et al., "Modified Gangliosides as a Possible Modulatosr of Transmembrane Signalling Merchandism Through Growth Factor Receptors: A Preliminary Note", Biochemical Biophysical Research Communniction, 147(1), 127–134, (1987).
Hirabayashi, Y., et al., "Isolation and Characterization of Extremely Minor Gangliosides, Gm1b and $G_{D1\alpha}$ in Adult Bovine Brains as Developmentally Regulated", Journal of Biological Chemistry, 265(14), 8144–8151, (1990).
Leeden, R.W., "Biology of Gangliosides: Neuritogenic and Neuronotrophic Properties", Journal of Neuroscience Research, 12, 147–159, (1984).
Matta, S.G., et al., "Neuritogenic and Metabolic Effects of Individual Gangliosides and Their Intereaction With Nerve Growth Factor in Cultures of Neuroblastoma and Pheochromocytoma", Development Brain Research, 27(½), 243–252, (1986).
Nores, G.A., et al., "Density–Dependent Recognition of Cell Surface $GM_3$ by a Certain Anti–melanoma Antibody, and $GM_3$ Lactone as a Possible Immunogen: Requirements for Tumor–associated Antigen and Immunogen", Journal of Immunology, 139(1), 3171–3176, (1992).
Rebbaa, A., et al., "Ganglioside GM3 Inhibition of EGF Receptor Mediated Signal Transduction", Glycobiology, 6(4), 399–406, (1996).
Sharon, N., et al., "Lectins as Cell Recognition Molecules", Science, 266, 227–234, (1989).
Taki, T., et al., "A Ganglioside of Rat Ascites Hepatoma AH 7974F Cells", Journal of Biological Chemistry, 261(7), 3075–3078, (1986).

(List continued on next page.)

Primary Examiner—Howard C. Lee
(74) Attorney, Agent, or Firm—Schwegman, Lundberg, Woessner & Kluth, P.A.

(57) ABSTRACT

The invention provides versatile sialic acid C-glycoside precursors that are useful for preparing C-glycoside analogs of Gangliosides, peptides, and proteins, as well as synthetic intermediates useful for the preparation of the precursors, and synthetic methods useful for preparing the precursors and the intermediates. The invention also provides gangliosides, peptides, and proteins that comprise sialic acid C-glycoside components, as well as synthetic methods useful for the preparation of such compounds.

24 Claims, 8 Drawing Sheets

OTHER PUBLICATIONS

Tulay, P., et al., "A General Method for the Stereospecific Synthesis of C–Glycosides of Ulosonic Acids by Samarium–Mediated Reductive Dechlorination", *Synlett*, 1195–1196, (Nov. 1998).

Varki, A., "Diversity in the Sialic Acids", *Glycobiology*, 2(1), 25–40, (1992).

Vlahov, I.R., et al., "Diastereocontrolled Synthesis of Carbon Glycosides of N–Acetylneuraminic Acid Via Glycosl Samarium (III) Intermediate", *Journal of the American Chemical Society*, 119(6), 1480–1481.

Yamakawa, T., et al., "The Chemistry of the Lipids of Posthemolytic Residue or Stroma of Erythrocytes. III. Globoside, The Sugar –containing Lipid of Human Blood Stroma", *Journal of Biochemistry*, 39(4), 393–402, (1952).

Yang, L.J., et al., "Gangliosides are Neuronal Ligands for Myelin–associated Glycoprotein", Proceedings of the National Academy of Sciences USA, 93(2), 814–814, (1996).

* cited by examiner

C-GLYCOSIDE ANALOGS AND METHODS FOR THEIR PREPARATION AND USE

BACKGROUND OF THE INVENTION

Gangliosides are cell-surface sialic acid containing glycolipids. They are found in high concentration on the surface of central nervous system cells. Gangliosides are believed to play a role in important biological events such as cell growth regulation, cell-cell adhesion and malignancy (Taki, T., et al., *J. Biol. Chem*, 1986, 261, 3075–3078; Hirabayashi, Y., et al., *J. Biol. Chem*, 1990, 265, 8144–8151; atta, S. G., et al., *J Develop. Brain Res.*, 1986, 27, 243–252; and Leeden, R. W. *J. Neurosci. Res.* 1984, 12, 147). Gangliosides typically consist of fatty acids (e.g. steric acid) sphingosine, hexoses (e.g. galactose and glucose), galactosamine, and sialic acids (*The Merck Index*, 10 ed., 1983B, Martha Windholz ed., Merck Co. Inc., Rahway, N.J., U.S.A., p 623 (4227)).

GM4 (1, FIG. 1) is structurally the simplest ganglioside, and has been isolated as a minor component from brain, rat kidney, mouse erythrocytes and chicken egg yolk (Hakamori, S. in *Handbook of Lipid research*, Vol. 3, *Sphingolipid Biochemistry;* Kanfer, J. N., Hakamori S., Eds; Plenum Press: New York, pp 99–101 (1983); Hakamori, S. *Annu. Rev. Biochem.*, 1981, 5, 733–764; and Nores, G. A., et al., *J. Immunol.*, 1987, 139, 3171–3176). GM4 is an important cell adhesion molecule in cell growth and tissue regeneration, and promotes neuron adhesion through its interaction with myelin-associated glycoprotein (Yang, L. J., et al., *Proc. Nat. Acad. Sci. USA* 1996, 93, 814–818).

GM3 (2, FIG. 1) was first isolated from equine erythrocytes and is known to modulate the epidermal growth factor (EGF) and the platelet-derived growth factor (PDGF) receptors. Tumors, such as those involved in brain cancer, overexpress EGF receptor. GM4 and GM3 are also found in high concentration in tumor cells (Yamakawa, T.; Suzuki, S. J. *Biochem* 1952, 39, 383–402; Rebbaa, A., et al., *Glycobiology* 1996, 6, 399–406; Bremer, E., et al., *J. Biol. Chem*, 1986, 261, 2434–2440; Hanai, N., et al., *Biochem. Biophys. Res. Commun.* 1987, 147, 127–134; and Carubia, J. M., et al., *Biochem. Biophys. Res. Commun.* 1984, 120, 500–504).

The sialic acid N-Acetylneuraminic acid is often found at the non-reducing end of the oligosaccharide component of gangliosides. N-Acetylneuraminic acid is involved in a number of important biological events including: intracellular interactions such as adhesion, aggregation and agglutination; mask of antigenic oligosaccharides and suppression of undesired immune reactions; influence on the cell membrane permeability for ions, amino acids and proteins; and protection of glycoproteins against proteolysis (*Sialic Acids;* Schauer, R. (Ed.); Springer-Verlag: New York, 1985; *Biological Roles of Sialic Acid;* Rosenberg, V.; Shengrund, C. (Eds.); Plenum; New York, 1976; Sharon, N. *Complex carbohydrates;* Addison-Wesley: London, 1975; and Varki, A. *Glycobiology*, 1992, 2, 25–40). Terminal N-acetylneuraminic acid is an attachment site of pathogens to the cells and often, the removal of this carbohydrate initiates catabolic and inflammatory processes (Sharon, N.; Lis, H. *Science*, 1989, 266, 227–234; Lis, H. *Lectins;* Chapman and Hall: London, 1989).

In vivo, sialic acid containing glycoconjugates are catabolized by the removal of the terminal sialic acid residue through the action of hydrolase type enzymes called neuraminidases that cleave the glycosidic bond of N-acetylneuraminc acid (Air, G. M.; Laver, W. *Proteins: Structure, Function and Genetics*, 1989, 6, 341–356). Thus, analogs of sialic acid containing glycoconjugates having a diminished susceptibility to such catabolism would be expected to have increased biological half-lives, and as a result, would be expected to possess significant therapeutic potential. Therefore, the design of nonhydrolyzable analogs of N-acetylneuraninic acid glycosides may provide a useful means to control, at the molecular level, events of crucial importance to glycobiology and immunology.

For example, analogs of GM4, having improved half-lives would be expected to demonstrate stable cell adhesion over a prolonged period of time (Yang, L. J., et al., *Proc. Nat. Acad. Sci. USA* 1996, 93, 814–818). Additionally, analogs of GM3 (4, Scheme 1) having prolonged half-lives would be expected to inhibit EGF receptor mediated signal transduction (Rebbaa, A., et al., *Glycobiology* 1996, 6, 399–406).

Vlahov, I. R., et al., *J. Am. Chem. Soc.*, 1997, 119, 1480–1481 described the synthesis of methyl 5-acetamido-4,7,8,9-tetra-O-acetyl-2,6-anhydro-3,5-dideoxy-2-C-{(R)-hydroxy-[3-(methyl 2,4,6-tri-O-benzyl-3-deoxy-α-D-galactopyranosidyl)]-methyl}-D-erythro-L-manno-nonate. However, attempts to use this C-disaccharide as a building block for the synthesis of analogs of GM3 and GM4 by converting the anomeric methyl group into acetate or thiophenyl failed.

Thus, there is currently a need for synthetic methods and synthetic precursors that can be used to prepare ganglioside C-glycoside analogs, as well as other glycoconjugates (e.g. glycopeptides and glycoproteins) with improved therapeutic potential (e.g. improved stability or pharmacodynamics).

SUMMARY OF THE INVENTION

The invention provides synthetic precursors (e.g. compound 22, FIG. 3) that are useful for preparing C-glycoside analogs of gangliosides (e.g. GM1–GM4), peptides, and proteins. The invention also provides synthetic methods useful for preparing such synthetic precursors, as well as compounds useful as intermediates for the preparation such synthetic precursors.

The invention provides a compound of formula I:

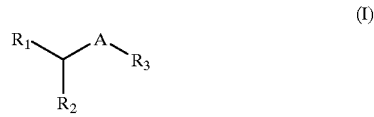

wherein:

$R^1$ is the residue of a sialic acid;

$R_2$ is hydrogen, hydroxy, or $(C_1-C_6)$alkanoyloxy;

$R_3$ is arylthio, optionally substituted on the aryl ring with 1, 2, 3, or 4 substituents independently selected from the group consisting of halo, nitro, cyano, trifluoromethoxy, $(C_1-C_6)$alkyl, $(C_1-C_6)$alkoxy, $(C_1-C_6)$alkanoyl, halo$(C_1-C_6)$alkyl, hydroxy$(C_1-C_6)$alkyl, $(C_1-C_6)$alkoxycarbonyl, $(C_1-C_6)$alkylthio, and $(C_1-C_6)$alkanoyloxy; and A is the residue of a monosaccharide.

The invention provides a compound of formula 22a:

![compound 22a structure]

wherein:

Ra is aryl, optionally substituted with 1, 2, 3, or 4 substituents independently selected from the group consisting of halo, nitro, cyano, trifluoromethoxy, $(C_1-C_6)$alkyl, $(C_1-C_6)$alkoxy, $(C_1-C_6)$alkanoyl, halo$(C_1-C_6)$alkyl, hydroxy$(C_1-C_6)$alkyl, $(C_1-C_6)$alkoxycarbonyl, $(C_1-C_6)$alkylthio, and $(C_1-C_6)$alkanoyloxy;

each Rb is independently a suitable hydroxy protecting group;

Rc is $(C_1-C_6)$alkyl;

Rd is a suitable hydroxy protecting group;

each Re is independently a suitable hydroxy protecting group; and

Rf is $(C_1-C_6)$alkanoyl.

The invention provides a ganglioside that comprises a C-glycoside component of formula II:

$$R_1 \diagdown_{R_2} A \qquad (II)$$

wherein:

$R_1$ is the residue of a sialic acid;

$R_2$ is hydrogen, hydroxy, or $(C_1-C_6)$alkanoyloxy; and

A is the residue of a monosaccharide.

The invention provides a method for preparing compound 22:

![compound 22 structure]

comprising reacting a compound of formula 21:

![compound 21 structure]

with thiophenol.

The invention provides a method for preparing a compound of formula 22a:

![compound 22a structure]

wherein:

Ra is aryl, optionaly substituted with 1, 2, 3, or 4 substituents independently selected from the group consisting of halo, nitro, cyano, trifluoromethoxy, $(C_1-C_6)$alkyl, $(C_1-C_6)$alkoxy, $(C_1-C_6)$alkanoyl, halo$(C_1-C_6)$alkyl, hydroxy$(C_1-C_6)$alkyl, $(C_1-C_6)$alkoxycarbonyl, $(C_1-C_6)$alkylthio, and $C_1-C_6)$alkanoyloxy;

each Rb is independently a suitable hydroxy protecting group;

Rc is $(C_1-C_6)$alkyl;

Rd is a suitable hydroxy protecting group;

each Re is independently a suitable hydroxy protecting group; and

Rf is $(C_1-C_6)$alkanoyl;

comprising reacting a corresponding compound of formula 21a:

![compound 21a structure]

wherein Rg is aryl, optionally substituted with 1, 2, 3, or 4 substituents independently selected from the group consisting of $(C_1-C_6)$alkoxy;

with the requsite arylthiol, to provide the compound of formula 22a.

The invention provides a method for preparing Neu5Acα3GalCer (3) comprising: hydrolyzing the methyl ester of a compound of formula 28:

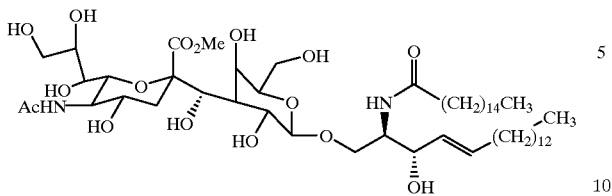

28 to provide the compound of formula 3.

The invention provides a method for preparing Neu5Acα3Galβ4GlcCer (4) comprising hydrolyzing the methyl ester of compound of formula 31:

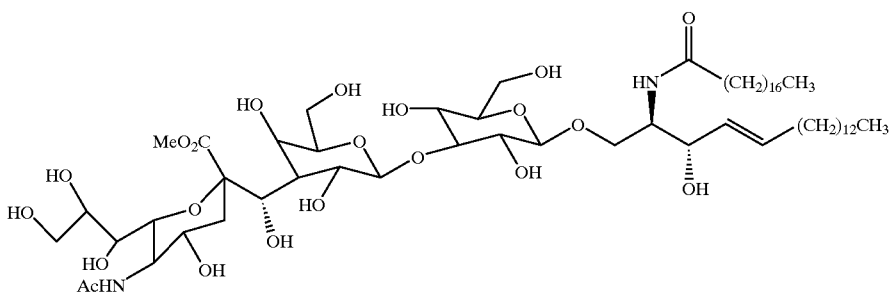

31 to provide the compound of formula 4.

The invention provides a method for preparing a compound of formula 3a wherein $R_m$ is $(C_1-C_6)$alkanoyl; comprising hydrolyzing the ester of a compound of formula 28a:

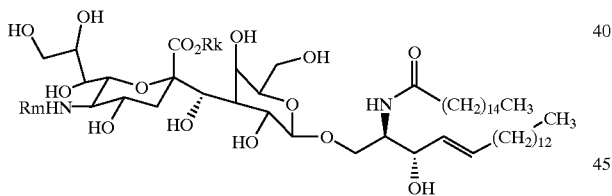

28a wherein $R_k$ is $(C_1-C_6)$alkyl, to provide the compound of formula 3a.

The invention provides a method for preparing a compound of formula 4a:

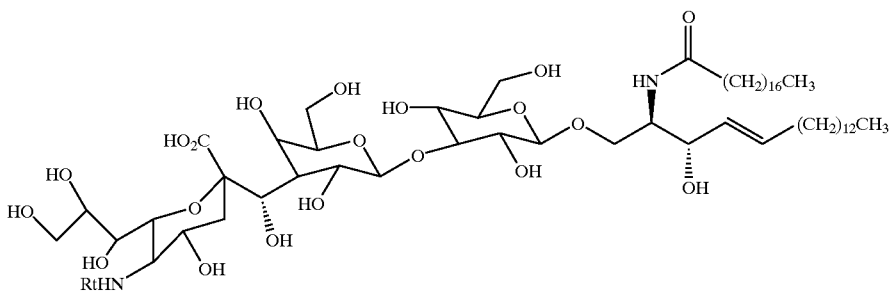

4a wherein $R_t$ is $(C_1-C_6)$alkanoyl, comprising hydrolyzing the ester of compound of formula 31a:

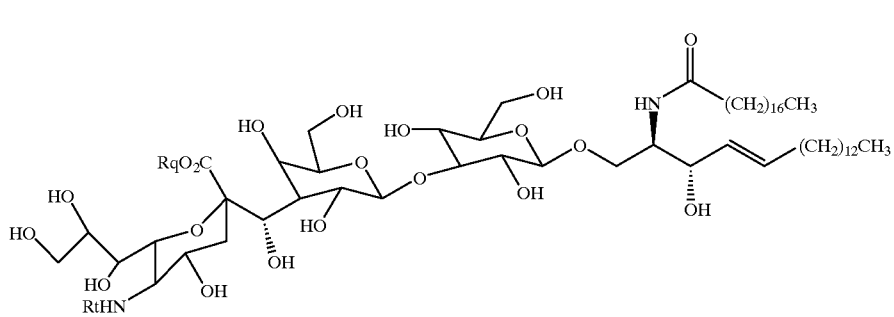

wherein $R_t$ is $(C_1-C_6)$alkyl, to provide the compound of formula 4a.

The invention also provides a compound of formula 3a, 4a, 18, 19, 20, 21, 22, 18a, 19a, 21a, 22a, 22b, 22c, 24, 25, 26, 27, 28, 30, 31, 24a, 25a, 26a, 27a, 28a, 30a, or 31a as well as methods for preparing such a compound.

The invention also provides a method for preparing the C-glycoside of Neu5Acα3GalCer 3 comprising O-glycosylating a compound of formula 22 or an activated derivative thereof with ceramic acid, and deprotecting to provide 3. Suitable activated derivatives of a compound of formula 22 include the corresponding thioglycosides, sulfoxides, trichloroacetimidates, glycosyl halides, epoxides, reducing sugars, glycosylphosphorous derivatives, and anomeric acetates. Methods for preparing such derivatives are known in the art (see for example, Barresi, F., Hindsgaul, O., J. Carbohydr. Chem., 1995, 14, 1043–1087, and references cited therein).

Similarly, the invention also provides a method for preparing Neu5Acα3Galβ4GlcCer 4 comprising O-glycosylating a compound of formula 22 or an activated derivative thereof with a suitably protected glucose, activating the anomeric position of the glucose, and O-glycosylating with ceramic acid to provide compound 4. Suitable methods for activating the anomeric position of the glucose are known in the art (see for example, Barresi, F., Hindsgaul, O., J. Carbohydr. Chem., 1995, 14, 1043–1087, and references cited therein).

The invention also provides a method for treating or preventing cancer comprising administering to a mammal in need of such therapy, a ganglioside that comprises a C-glycoside component of formula II (e.g. compound 3 or 4).

The invention provides a ganglioside that comprises a C-glycoside component of formula II for use in medical therapy, as well as the use of such a ganglioside for the manufacture of a medicament for the treatment or prevention of cancer.

BRIEF DESCRIPTION OF THE FIGURES

FIG. 4 illustrates the synthesis of compound 22a.

FIG. 7 illustrates the synthesis of compound 3a.

FIG. 8 illustrates the synthesis of compound 4a.

DETAILED DESCRIPTION

Figure 1:
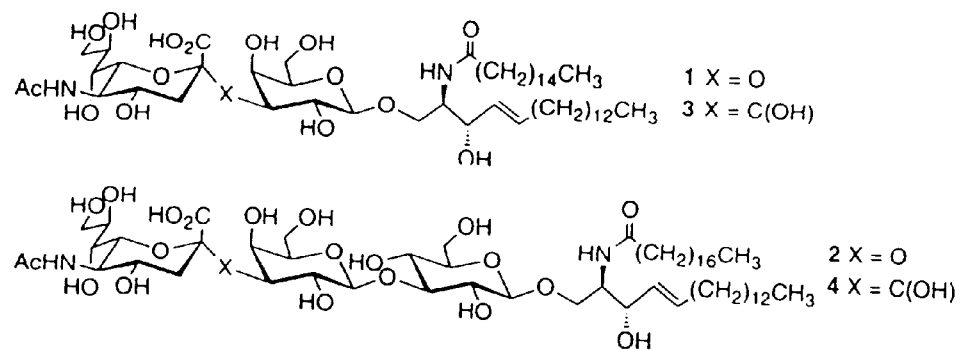
FIG. 1 illustrates gangliosides GM4 (1) and GM3 (2), as well as compounds of the invention 3 and 4.

The following definitions are used, unless otherwise described: halo is fluoro, chloro, bromo, or iodo. Alkyl, alkoxy, etc. denote both straight and branched groups; but reference to an individual radical such as "propyl" embraces only the straight chain radical, a branched chain isomer such as "isopropyl" being specifically referred to. Aryl denotes a phenyl radical or an ortho-fused bicyclic carbocyclic radical having about nine to ten ring atoms in which at least one ring is aromatic. Heteroaryl encompasses a radical attached via a ring carbon of a monocyclic aromatic ring containing five or six ring atoms consisting of carbon and one to four heteroatoms each selected from the group consisting of non-peroxide oxygen, sulfur, and N(X) wherein X is absent or is H, O, $(C_1-C_4)$alkyl, phenyl or benzyl, as well as a radical of an ortho-fused bicyclic heterocycle of about eight to ten ring atoms derived therefrom, particularly a benzo-derivative or one derived by fusing a propylene, trimethylene, or tetramethylene diradical thereto.

It will be appreciated by those skilled in the art that compounds of the invention having a chiral center(s) may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase).

As used herein a "residue of a sialic acid" is a sialic acid molecule or protected derivative thereof having an open valence for bonding to the remainder of a compound of formula I or formula II. Such a residue can be formed by removing a hydrogen, hydroxy or other functional group from a corresponding sialic acid molecule. One example of a sialic acid residue is a compound of the following formula:

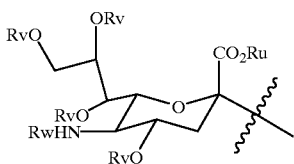

wherein Ru is hydrogen or (C$_1$–C$_6$)alkyl; each Rv is independently a suitable hydroxy protecting group; and Rw is hydrogen or (C$_1$–C$_6$)alkanoyl.

As used herein a "residue of a monosaccharide is a monosaccharide molecule or protected derivative thereof having two open valences for bonding to the remainder of a compound of formula I. Such a residue can be formed by removing one or two a hydrogen, hydroxy or other functional group from a corresponding monosaccharide molecule. One example of such a residue of a monosaccharide is a compound of the following formula:

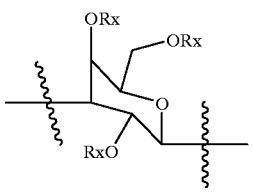

wherein each Rx is independently hydrogen or a suitable hydroxy protecting group.

Specific and preferred values listed below for radicals, substituents, and ranges, are for illustration only; they do not exclude other defined values or other values within defined ranges for the radicals and substituents Specifically, (C$_1$–C$_6$)alkyl can be methyl, ethyl, propyl, isopropyl, butyl, iso-butyl, sec-butyl, pentyl, 3-pentyl, or hexyl; (C$_1$–C$_6$)alkoxy can be methoxy, ethoxy, propoxy, isopropoxy, butoxy, iso-butoxy, sec-butoxy, pentoxy, 3-pentoxy, or hexyloxy; (C$_1$–C$_6$)alkanoyl can be acetyl, propanoyl or butanoyl; halo(C$_1$–C$_6$)alkyl can be iodomethyl, bromomethyl, chloromethyl, fluoromethyl, trifluoromethyl, 2-chloroethyl, 2-fluoroethyl, 2,2,2-trifluoroethyl, or pentafluoroethyl; hydroxy(C$_1$–C$_6$)alkyl can be hydroxymethyl, 1-hydroxyethyl, 2-hydroxyethyl, 1-hydroxypropyl, 2-hydroxypropyl, 3-hydroxypropyl, 1-hydroxybutyl, 4-hydroxybutyl, 1-hydroxypentyl, 5-hydroxypentyl, 1-hydroxyhexyl, or 6-hydroxyhexyl; (C$_1$–C$_6$) alkoxycarbonyl can be methoxycarbonyl, ethoxycarbonyl, propoxycarbonyl, isopropoxycarbonyl, butoxycarbonyl, pentoxycarbonyl, or hexyloxycarbonyl; (C$_1$–C$_6$)alkylthio can be methylthio, ethylthio, propylthio, isopropylthio, butylthio, isobutylthio, pentylthio, or hexylthio; (C$_2$–C$_6$) alkanoyloxy can be acetoxy, propanoyloxy, butanoyloxy, isobutanoyloxy, pentanoyloxy, or hexanoyloxy; aryl can be phenyl, indenyl, or naphthyl; and heteroaryl can be furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide) or quinolyl (or its N-oxide).

A specific value for R$_1$ is a residue of neuraminic acid, 3-deoxy-D-glycero-D-galacto-2-nonulosonic acid, or 3-deoxy-D-manno-2-octulosonic acid.

A specific value for R$_1$ is methyl-5-acetamido-4,7,8,9-tetra-O-acetyl-3,5-dideoxy-D-glycero-α-D-galacto-non-2-ulopyranosyl)onate.

A specific value for A is a glucose or galactose residue.

A specific value for A is phenyl 2,4,6tri-O-acetyl-3-deoxy-thio-β-D-galacto-pyranosid-3-yl.

A specific group of compounds of formula I are compounds wherein R$_3$ is bonded to the anomeric carbon of A.

A specific value for R$_3$ is phenylthio.

A specific compound of formula I is methyl 5-acetamido-4,7,8,9-tetra-O-acetyl-2,6-anhydro-3,5-dideoxy-2-C-{(R)-O-acetyl-[3-(phenyl 2,4,6-tri-O-acetyl-3-deoxy-thio-β-D-galacto-pyranosidy]methyl}-D-erythro-L-manno-nonate.

A specific compound of the invention is a compound of formula 18a:

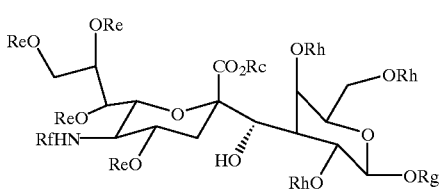

wherein:

Rc is (C$_1$–C$_6$)alkyl;

each Re is independently a suitable hydroxy protecting group;

Rf is (C$_1$–C$_6$)alkanoyl;

Rg is aryl, optionally substituted with 1, 2, 3, or 4 substituents independently selected from the group consisting of (C$_1$–C$_6$)alkoxy; and each Rh is independently a suitable hydroxy protecting group (e.g. a group that can be selectively removed in the presence of CO$_2$Rc, Rf and each Re).

A specific compound of the invention is a compound of formula 19a:

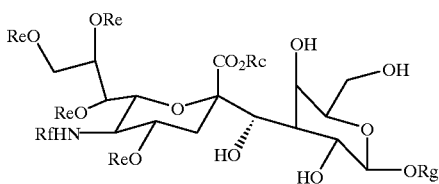

wherein

Rc is (C$_1$–C$_6$)alkyl;

each Re is independently a suitable hydroxy protecting group;

Rf is (C$_1$–C$_6$)alkanoyl; and

Rg is aryl, optionally substituted with 1, 2, 3, or 4 substituents independently selected from the group consisting of (C$_1$–C$_6$)alkoxy.

A specific compound of the invention is a compound of formula 21a:

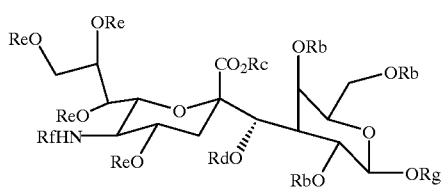

21a wherein each Rb is independently a suitable hydroxy protecting group;

Rc is $(C_1-C_6)$alkyl;

Rd is a suitable hydroxy protecting group;

each Re is independently a suitable hydroxy protecting group; and

Rf is $(C_1-C_6)$alkanoyl; and

Rg is aryl, optionally substituted with 1, 2, 3, or 4 substituents independently selected from the group consisting of $(C_1-C_6)$alkoxy.

A specific compound of the invention is a compound of formula 22b:

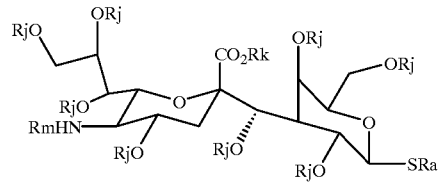

22b wherein $R_a$ is aryl, optionally substituted with 1, 2, 3, or 4 substituents independently selected from the group consisting of halo, nitro, cyano, trifluoromethoxy, $(C_1-C_6)$alkyl, $(C_1-C_6)$alkoxy, $(C_1-C_6)$alkanoyl, halo$(C_1-C_6)$alkyl, hydroxy$(C_1-C_6)$alkyl, $(C_1-C_6)$alkoxycarbonyl, $(C_1-C_6)$alkylthio, and $(C_1-C_6)$alkanoyloxy; each $R_j$ is independently a suitable hydroxy protecting group; $R_k$ is $(C_1-C_6)$alkyl; and $R_m$ is $(C_1-C_6)$alkanoyl.

A specific compound of the invention is a compound of formula 24a:

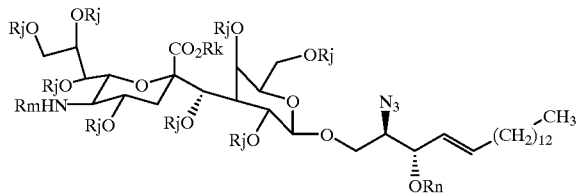

24a wherein: each $R_j$ is independently a suitable hydroxy protecting group; $R_k$ is $(C_1-C_6)$alkyl; $R_m$ is $(C_1-C_6)$alkanoyl; and $R_n$ is a suitable hydroxy protecting group.

A specific compound of the invention is a compound of formula 25a:

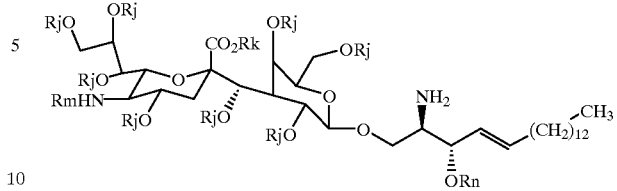

25a wherein each $R_j$ is independently a suitable hydroxy protecting group; $R_k$ is $(C_1-C_6)$alkyl; $R_m$ is $(C_1-C_6)$alkanoyl; and $R_n$ is a suitable hydroxy protecting group.

A specific compound of the invention is a compound of formula 26a:

26a

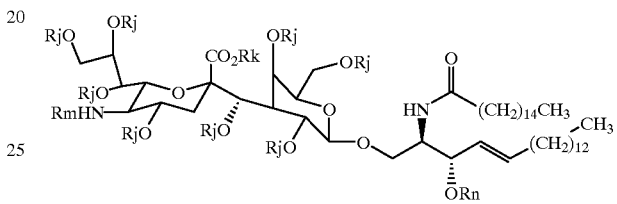

wherein each $R_j$ is independently a suitable hydroxy protecting group; $R_k$ is $(C_1-C_6)$alkyl; $R_m$ is $(C_1-C_6)$alkanoyl; and $R_n$ is a suitable hydroxy protecting group (e.g. a group that can be selectively removed in the presence of $R_j$, $R_k$, and $R_m$).

A specific compound of the invention is a compound of formula 27a:

27a

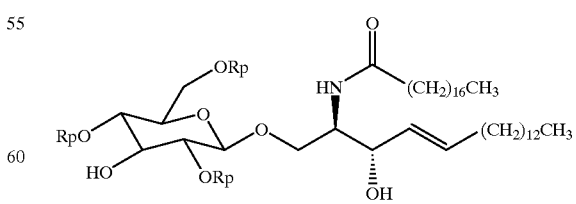

wherein each $R_j$ is independently a suitable hydroxy protecting group; $R_k$ is $(C_1-C_6)$alkyl; and $R_m$ is $(C_1-C_6)$alkanoyl.

A specific compound of the invention is a compound of formula 29a:

29a wherein each $R_p$ is independently a suitable hydroxy protecting group.

A specific compound of the invention is a compound of formula 30a:

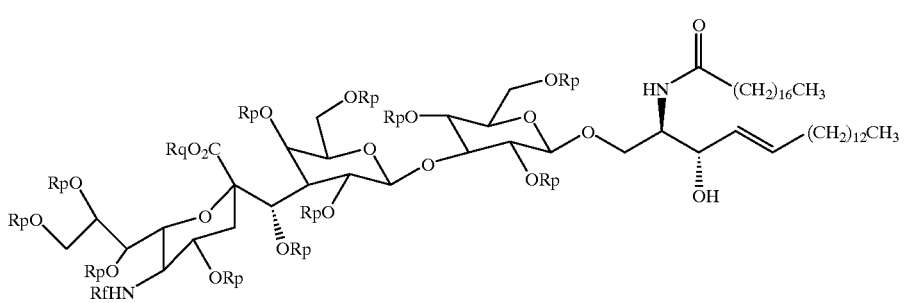

30a wherein each $R_p$ is independently a suitable hydroxy protecting group; $R_q$ is $(C_1-C_6)$alkyl; and $R_t$ is $(C_1-C_6)$alkanoyl.

A specific compound of the invention is a compound of formula 22c:

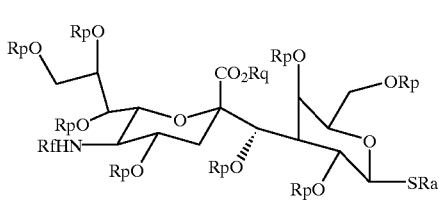

22c wherein Ra is aryl, optionally substituted with 1, 2, 3, or 4 substituents independently selected from the group consisting of halo, nitro, cyano, trifluoromethoxy, $(C_1-C_6)$alkyl, $(C_1-C_6)$alkoxy, $(C_1-C_6)$alkanoyl, halo$(C_1-C_6)$alkyl, hydroxy$(C_1-C_6)$alkyl, $(C_1-C_6)$alkoxycarbonyl, $(C_1-C_6)$alkylthio, and $(C_1-C_6)$alkanoyloxy; each $R_p$ is independently a suitable hydroxy protecting group; $R_q$ is $(C_1-C_6)$ alkyl; and $R_t$ is $(C_1-C_6)$alkanoyl.

The invention provides a ganglioside that comprises a C-glycoside component of formula II. The C-glycoside component of formula II can conveniently be linked to a gangleoside, or can replace a corresponding O-glycoside component of a ganglioside, to provide a ganglioside of the invention. Such synthetic transformations can be carried out using techniques that are known in the field of synthetic chemistry.

Specific gangliosides that comprises a C-glycoside component of formula II include: Neu5Acα3GalCer; Neu5Acα3Galβ4GlcCer; GalNAcβ4(Neu5Acα3) Galβ4GlcCer; Galβ3GalNAcβ4(Neu5Acα3)Galβ4GlcCer; Neu5Acα3Galβ3GalNAcβ4Galβ4GlcCer; Neu5Acα8Neu5Acα3Galβ4GlcCer; GalNAcβ4(Neu5Acα8 Neu5Acα3)Galβ4GlcCer; Neu5Acα3Galβ3GalNAcβ4 (Neu5Acα3)Galβ4GlcCer; Galβ3GalNAcβ4(Neu5Acα8 Neu5Acα3)Galβ4GlcCer; Neu5Acα8Neu5Acα3Galβ3GalNAcβ4(Neu5Acα3) Galβ4GlcCer; Neu5Acα3Galα3GalNAcβ4 (Neu5Acα8Neu5Acα3)Galβ4GlcCer; Galβ3GalNAcβ4 (Neu5Acα8 Neu5Acα8Neu5Acα3)Galβ4GlcCer; or Neu5Acα8Neu5Acα3Galβ3GalNAcβ4(Neu5Acα8-Neu5Acα3)Galβ4GlcCer;

Processes for preparing synthetic precursors of formula 22 and 22a are provided as further embodiments of the invention and are illustrated by the following procedures in which the meanings of the generic radicals are as given above unless otherwise qualified.

The 3-formyl galactoside intermediate 15 (FIG. 2) was synthesized following the procedure described by Kong, F.; Lu, D. Carbohydr. Res., 1990, 198, 141–148, and Schmidt, R. R.; Beyerbach, A. Liebiegs Ann. 1992, 983–986.

Figure 2:
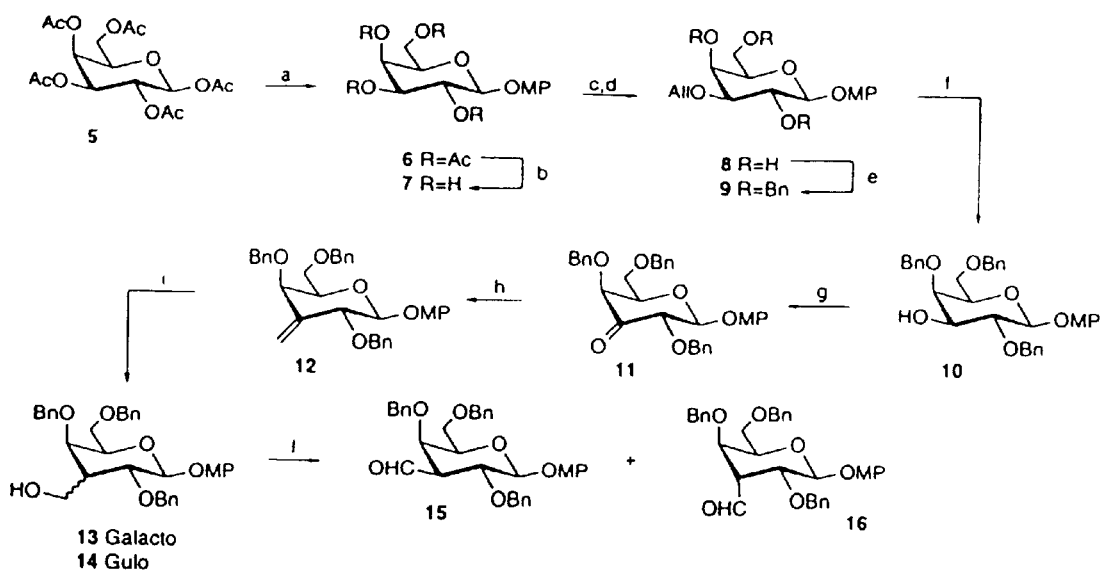
FIG. 2 illustrates the synthesis of intermediate 15.

As illustrated in FIG. 2, glycosidation of β-D-galactose pentaacetate 5 with p-methoxyphenol and trifluoromethanesulfonate as promoter (Murakata, C.; Ogawa, T. Carbohydr. Res., 1992, 235, 95–114), afforded the corresponding p-methoxyphenyl glycoside 6 in 92% yield. Deacetylation of 6, followed by regioselective allylation of the dibutyltin complex of 7, gave the corresponding 3-O-allyl galactopyranoside 8 in 85% yield. Benzylation of 8 under standard conditions (91%), followed by selective deallylation using palladium(II) chloride, afforded the 3-hydroxyl derivative 10 in 94% yield. Oxidation of 10 using DMSO-acetic anhydride (Albright, J. D.; Goldman, L. J. Am. Chem. Soc., 1965, 87, 4214–4216) gave to the corresponding 3-ketopyranoside 11 in 84% yield. Methylenation of 11 using Tebbe's reagent (Cannizzo, L. F.; Grubbs, R. H. J. Org. Chem., 1985, 50, 2386–2387) afforded the 3-methylene derivative 12 in 84% yield. Hydroboration of 12 using 9-BBN (Molino, B. F., et al., J. Carbohydr. Chem., 1987, 6, 479–493) led to a mixture of the corresponding 3-hydroxymethylene galactopyranoside 13 and gulopyranoside 14, which were not easily separable by chromatography on silica gel.

These two epimers were obtained in a ratio galacto 13: gulo 14 of 1.5:1.0, as determined by $^1$H NMR spectroscopy. The configuration at C-3 was deduced from the large $J_{2,3}$ vicinal coupling constant (11.1 Hz) for the galacto epimer 13 and from the smaller $J_{2,3}$ vicinal coupling constant (5.5 Hz) for the gulo epimer 14. Oxidation of the mixture 13–14 with the system DMSO-oxalyl chloride-triethylamine afforded the 3-formyl galactopyranoside 15 and the 3-formyl gulopyranoside 16 in 60% and 13% yield, respectively. The two epimers 15 and 16 were easily separable by chromatography on silica gel and their configuration at C-3 was determined by $^1$H NMR spectroscopy. The high $J_{2,3}$ vicinal coupling constant of 11.1 Hz observed for 15 and the smaller $J_{2,3}$ vicinal coupling constant of 6.6 Hz observed for 16 allowed the unambiguous assignment of the galacto configuration in 15 and gulo configuration in 16. The ratio of the 3-formyl galacto and gulo derivatives 15 and 16 obtained upon oxidation of 13–14 ranged from 4.6:1.0 to 1.0:1.0. These variations in the ratio could be the result of a partial in situ epimerization of the 3-formyl group in presence of triethylamine.

Figure 3:
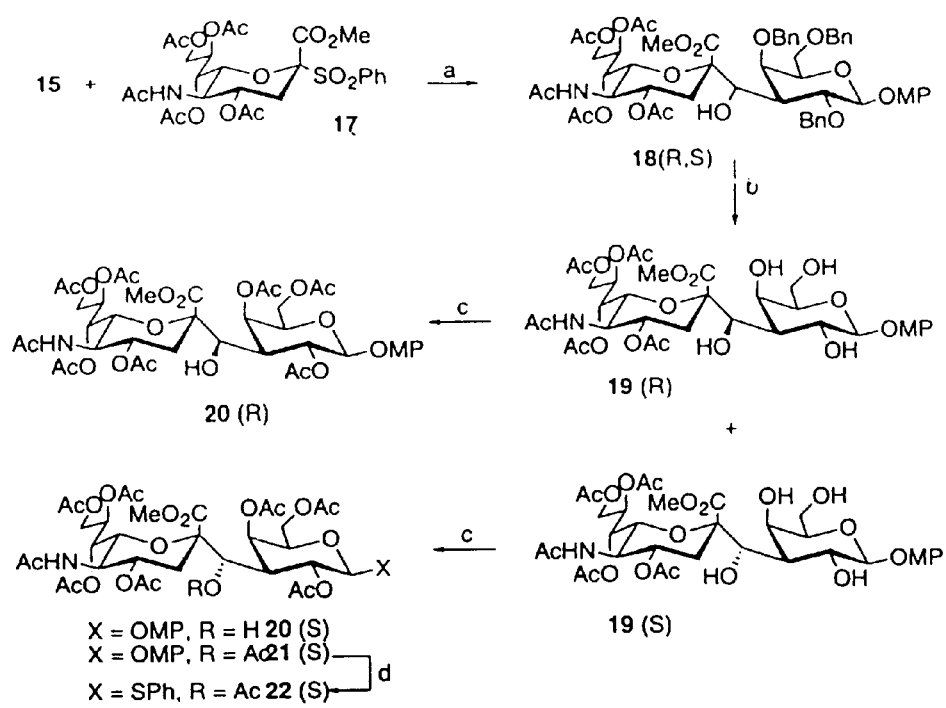
FIG. 3 illustrates the synthesis of compound 22.

Reaction of the 3-formyl galactoside 15 with the neuraminic acid sulfone 17 in presence of freshly prepared samarium(II) iodide afforded the corresponding C-disaccharides 18(R) and 18(S) (FIG. 3) in 85% yield. TLC of the reaction mixture indicated a diastereoisomeric ratio of approximately 4:1. However, the first minor isomer (R) was difficult to resolve from the second major isomer (S), decreasing its isolated yield and leading to an ratio R:S of 1.0:1.5. Standard debenzylation of the diastereoisomeric mixture 18(R)–18(S) afforded the corresponding disaccharides 19(R) and 19(S) in 90% yield, separable by chromatography on silica gel. Although both (R) and (S)-isomers could be isolated pure at this stage, the chirality of the hydroxymethylene bridge in each isomer could not easily be assigned from their $^1$H NMR spectra because of overlapping signals. Acetylation of the first isomer (19(R)) quantitatively afforded the corresponding acetylated derivative 20(R) having the free bridged hydroxyl, while acetylation of the second isomer (19(S)) under the same conditions quantitatively afforded the corresponding acetylated derivative 20(S) having the free bridged hydroxyl, together with some peracetylated derivative 21(S), the ratio 20(S):21(S) being 1.6:1.0. At this step, $^1$H NMR and 2D NOESY spectroscopy and molecular modeling were carried out to assign the hydroxymethlene stereochemistiy for 20 (R) and 20 (S). The $^1$H NMR spectrum of the first isomer (20(R)) displayed a coupling constant between the bridged proton and the proton H-3' of the galactose moiety ($J_{Hb,3'}$) of 2.7 Hz, while in the second isomer (20(S)), the same coupling was 5.2 Hz. Molecular modeling of the two diastereoisomers 20(R) and 20(S) used the package SYBYL (ver. 6.3) from Tripos Inc., St. Louis, Mo. All energy calculations were performed with parameters from the Tripos forcefield.

Charges were assigned according to the Gasteiger-Huckel protocol. A distance dependent dielectric ($\epsilon=4$) was used for chloroform as solvent. After energy minimization of both isomers, the torsion angle between the bridged carbon (Cb)-bridged hydrogen (Hb) bond and the carbon 3 (C-3')-proton 3 (H-3') bond of the galactose residue were determined. In the (R)-isomer, this torsion angle was approximately 60°, while in the (S)-isomer it was 180°. These two torsion angles corresponding to a smaller $J_{Hb,3'}$ coupling constant in the (R)-isomer than in the (S)-isomer, the chirality of the bridged carbon was assigned as (R) in the first isomer and as (S) in the second isomer. This assignment was further confirmed by the following observation. The molecular model of the (R)-isomer indicated that the equatorial proton H-3e of the neuraminic acid moiety pointed towards the bridged hydroxyl, implying that this equatorial proton should be downfield shifted in the $^1$H NMR spectrum of the (R)-isomer. In the (S) isomer, molecular modeling indicated that the axial proton H-3a of the neuraminic acid moiety pointed towards the bridged hydroxyl, implying a downfield shift of this proton in the $^1$H NMR spectrum of the (S)-isomer. The two chemical shifts expected for H-3e and H-3a of the neuraminic acid residue were in accordance with the experimental $^1$H NMR spectra of 20(R) and 20(S).

The assigned stereochemistry was further confirmed by 2D NOESY spectroscopy of 20(R) and 20(S). As expected, a strong NOE effect between bridge H/Gal H-3 for 20 (R) and bridge H/Gal H-2 for 20 (S) were observed. Differences are observed in the H-4' (Gal) chemical shifts of 20(R) and 20(S), 5.26 and 4.60 ppm, respectively. The signal at 1.78 ppm demonstrates the presence of a second shielded acetate in 20(S). These observations suggest the possible presence of an orthoacetate involving the bridge hydroxyl and 4-hydroxyl group of the neuraminic acid residue.

Removal of the p-methoxyphenyl glycoside in 20(R) was next attempted by selective oxidation using ceric ammonium nitrate (CAN) for 50 minutes at 0° C. FABMS spectroscopy of the resulting compound indicated the presence of two different molecular peaks, the first one at 793 ([M+NH$_4$]$^+$ 811, [M+Na]$^+$ 816, and [M+K]$^+$ 832), corresponding to the expecting molecular weight after p-methoxyphenyl removal, and the second one at 775 ([M+H]$^+$ 776), corresponding to an unsaturated derivative resulting from an elimination of p-methoxyphenol. $^1$H NMR spectroscopy of the same sample showed the presence of three anomeric protons between 6.2 and 6.4 ppm. One of these signals was consistent with the presence of a C1–C2 double bond in the galactose moiety. The large downfield chemical shifts observed for the two other anomeric protons indicated a possible acetyl migration to the anomeric position after p-methoxyphenyl removal. These two anomeric acetates could not be easily separated from the unsaturated derivative. The p-methoxyphenyl glycoside of the peracetylated derivative 21(S) was converted directly to the corresponding thiophenyl glycoside 22(S) in 73% yield by reaction of 21(S) with thiophenol and trifluoroboron etherate (Zhang, Z.; Magnusson, G. *Carbohydr. Res.*, 1996, 295, 41–55).

Figure 4:
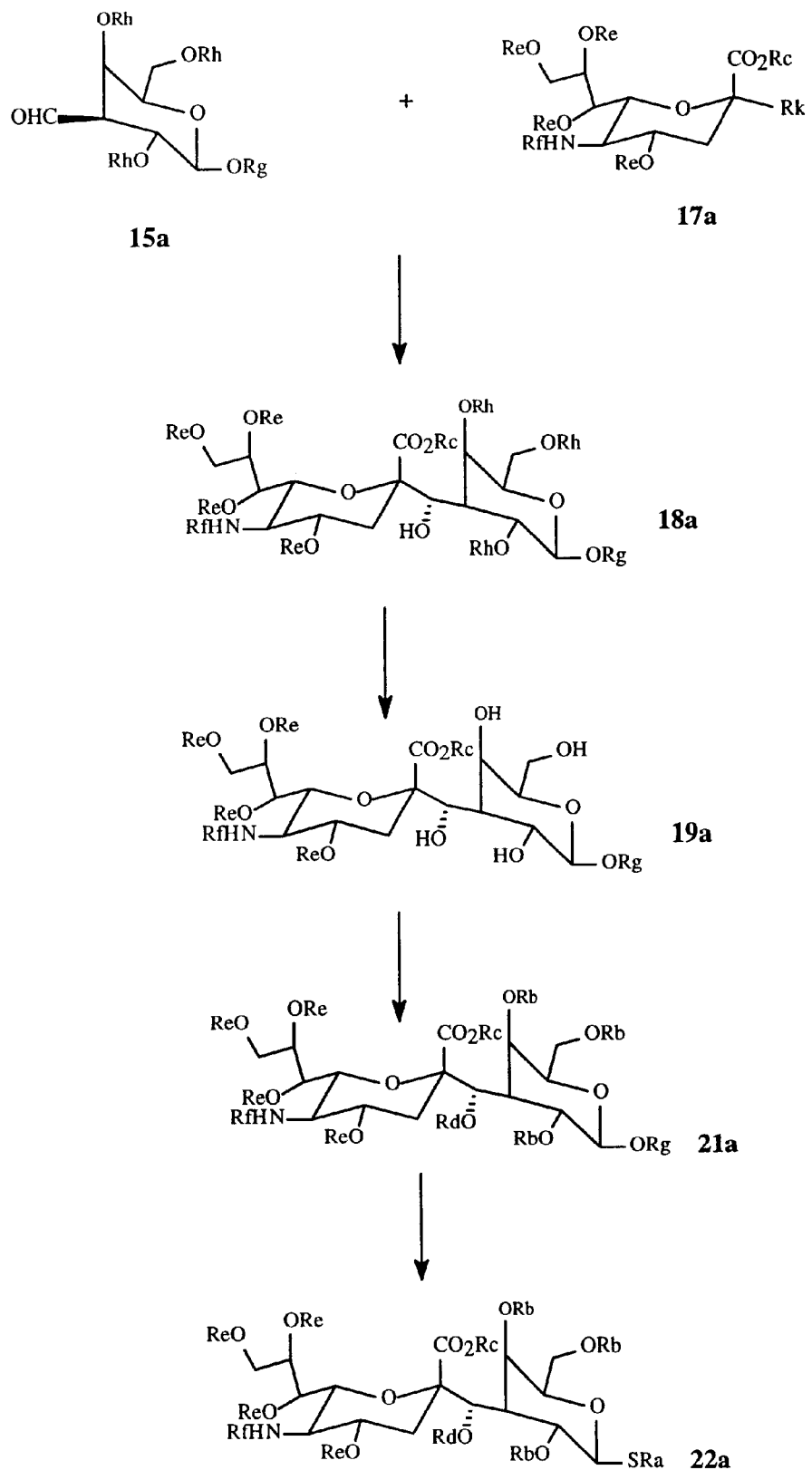

A synthetic precursor of formula 22a can generally be prepared as illustrated in FIG. 4. Reaction of sulfone 17a with aldehyde 15a in the presence of a lanthanide metal (e.g. SmI$_2$) provides a compound of formula 18a. The reaction can be carried out in any suitable solvent or combination of solvents, for example, in a hydrocarbon, a halogenated hydrocarbon, a linear or branched ether, or an ester. Specific solvents include benzene, toluene, chloroform, methylene chloride, diethyl ether, dioxane, and ethyl acetate. Preferably the reaction is carried out in tetrahydrofuran. The reaction can be carried out at any suitable temperature from the freezing point to the reflux temperature of the reaction mixture. Preferably the reaction is carried out at a temperature in the range of about 0° C. to about 50° C. More preferably at a temperature in the range of about 5° C. to about 25° C. The reaction can conveniently be carried out using conditions similar to those described in Example 1.

Selective removal of the protecting groups (Rh) from the compound of formula 18a yields a compound of formula 19a. Numerous protecting groups, as well as methods for their incorporation and removal, are known in the field of synthetic chemistry (see for example Greene, T. W.; Wutz, P. G. M. "Protecting Groups In Organic Synthesis" second edition, 1991, New York, John Wiley & sons, Inc; and). It will be appreciated by one skilled in the art that, for convenience, the protecting groups (Rc, Re, Rf, and Rh), in the compounds of formulae 15a and 17a should be selected so that the group(s) Rh can be selectively removed in their presence. One suitable combination of protecting groups is illustrated in the Examples hereinbelow (Rc=methyl, Re=acetyl, Rf=acetyl, and Rh=benzyl).

Protection of the hydroxy groups of the compound of formula 19a with suitable protecting groups Rb and Rd yields a compound of formula 21a. The reaction can conveniently be carried out using a procedure similar to that described in Example 4.

The conversion of a compound of formula 21a to a compound of formula 22a can be carried out under any suitable conditions. The reaction can be carried out in any suitable solvent or combination of solvents, for example, in a hydrocarbon, a halogenated hydrocarbon, or a linear or branched ether, or an ester. Specific solvents include benzene, toluene, chloroform, methylene chloride, diethyl ether, dioxane, and ethyl acetate. Preferably the reaction is carried out in toluene, in the presence of a Lewis acid catalyst (e.g. $BF_3.OEt_2$). The reaction can be carried out at any suitable temperature from the freezing point to the reflux temperature of the reaction mixture. Preferably the reaction is carried out at a temperature in the range of about 25° C. to about 100° C. More preferably at a temperature in the range of about 40° C. to about 75° C. The reaction can conveniently be carried out using conditions similar to those described in Example 5.

Figure 5:
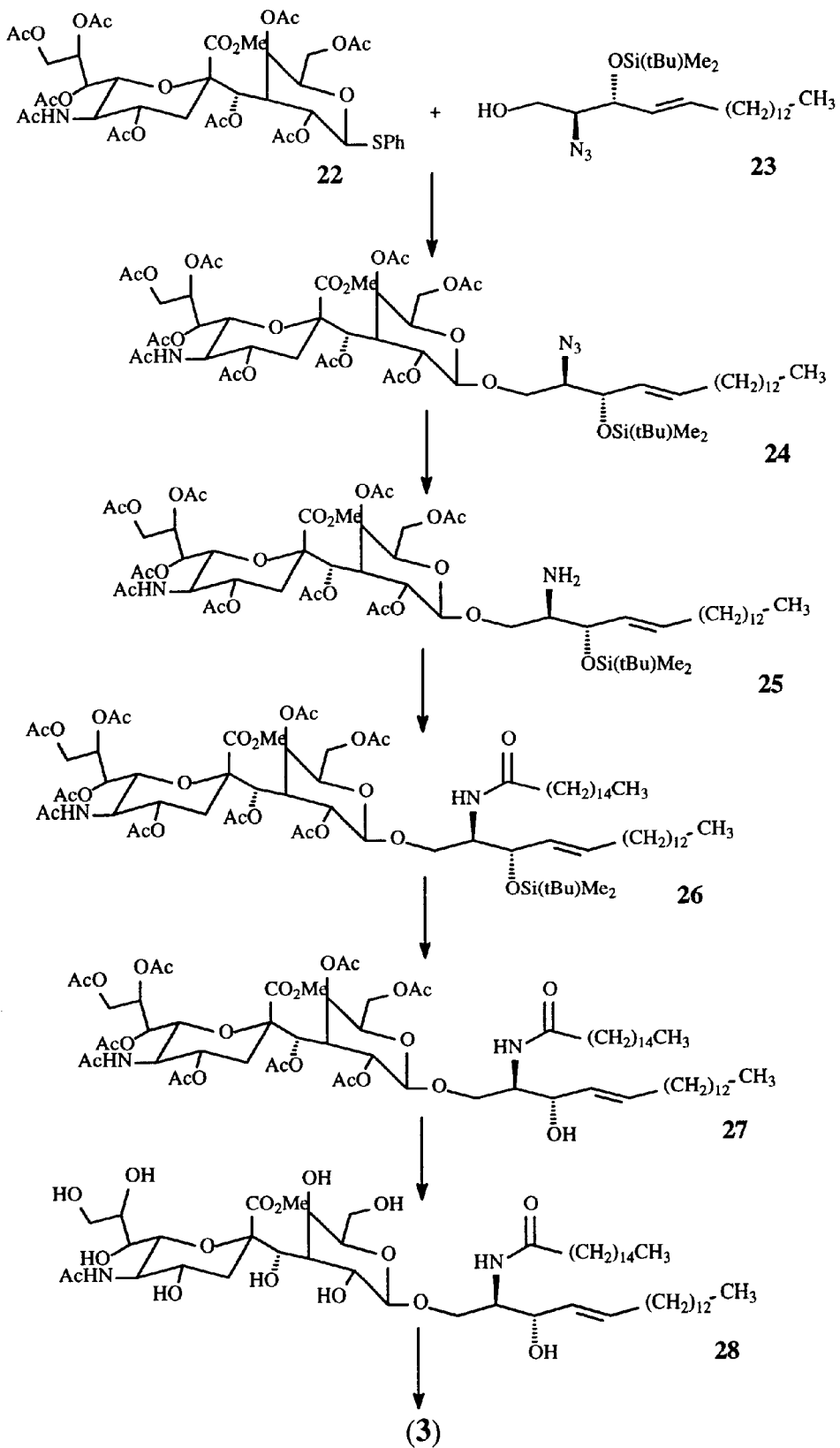
FIG. 5 illustrates the synthesis of compound 3.

As illustrated in FIG. 5, a compound of formula 3 can be prepared by reacting a compound of formula 22 with a compound of formula 23 to give a compound of formula 24. The reaction can be carried out in any suitable solvent or combination of solvents. For example, the reaction can conveniently be carried out in dichloromethane in the presence of a catalytic amount of silver triflate and tin (II) chloride. Reduction of the azide under standard conditions provides an amine of formula 25. The reduction can be carried out in any suitable solvent or combination of solvents, and can conveniently be carried out with $H_2S$ in pyridine. Acylation of the amine under standard conditions provides a compound of formula 26, which can be desilylated to provide an alcohol of formula 27. The reaction can be carried out in any suitable solvent or combination of solvents. For example, the reaction can be carried out with HF in pydidine. Compound 27 can be deacylated to give a compound of formula 28. The reaction can conveniently be carried out with sodium methoxide in methanol. Conversion of the ester 28 to a compound of formula 3 can be carried out under standard conditions, for example, with aqueous potassium hydroxide.

Figure 6:
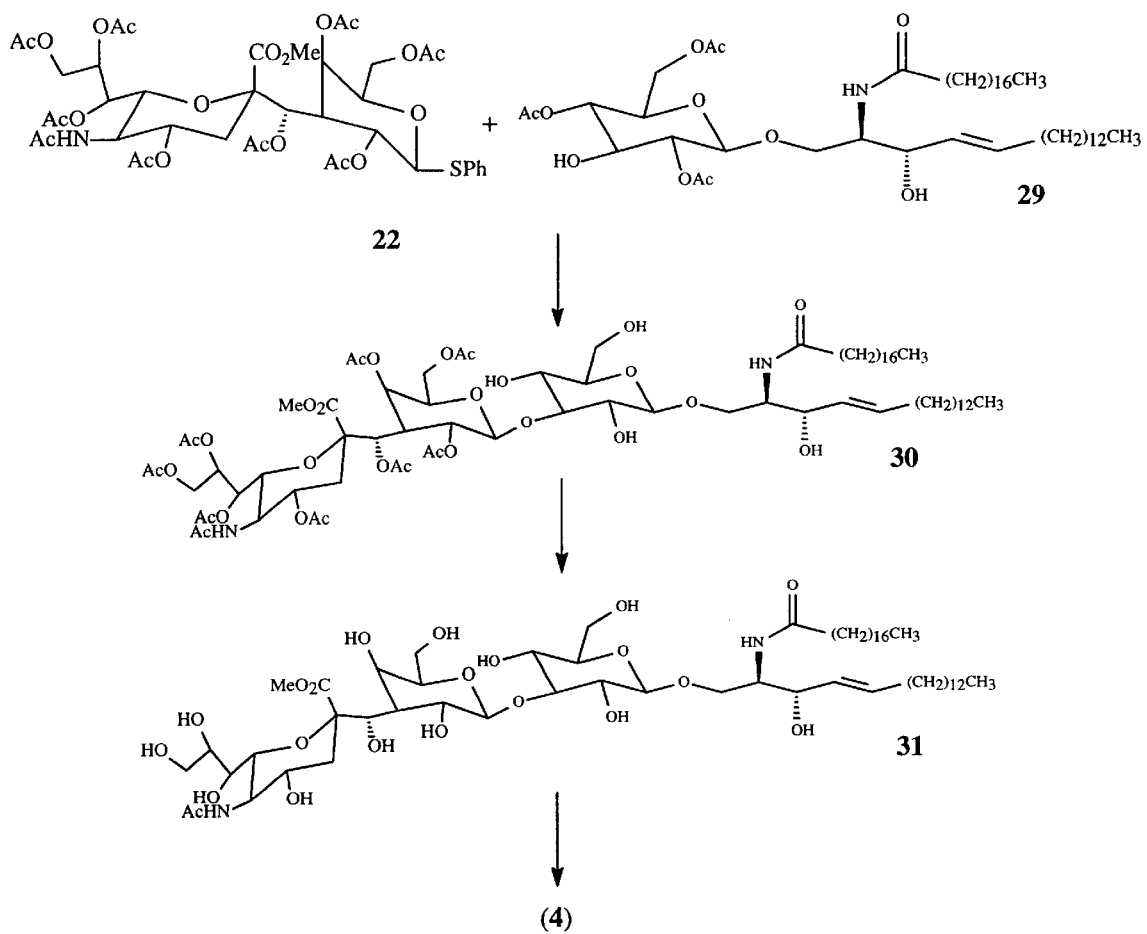
FIG. 6 illustrates the synthesis of compound 4.
Figure 7:
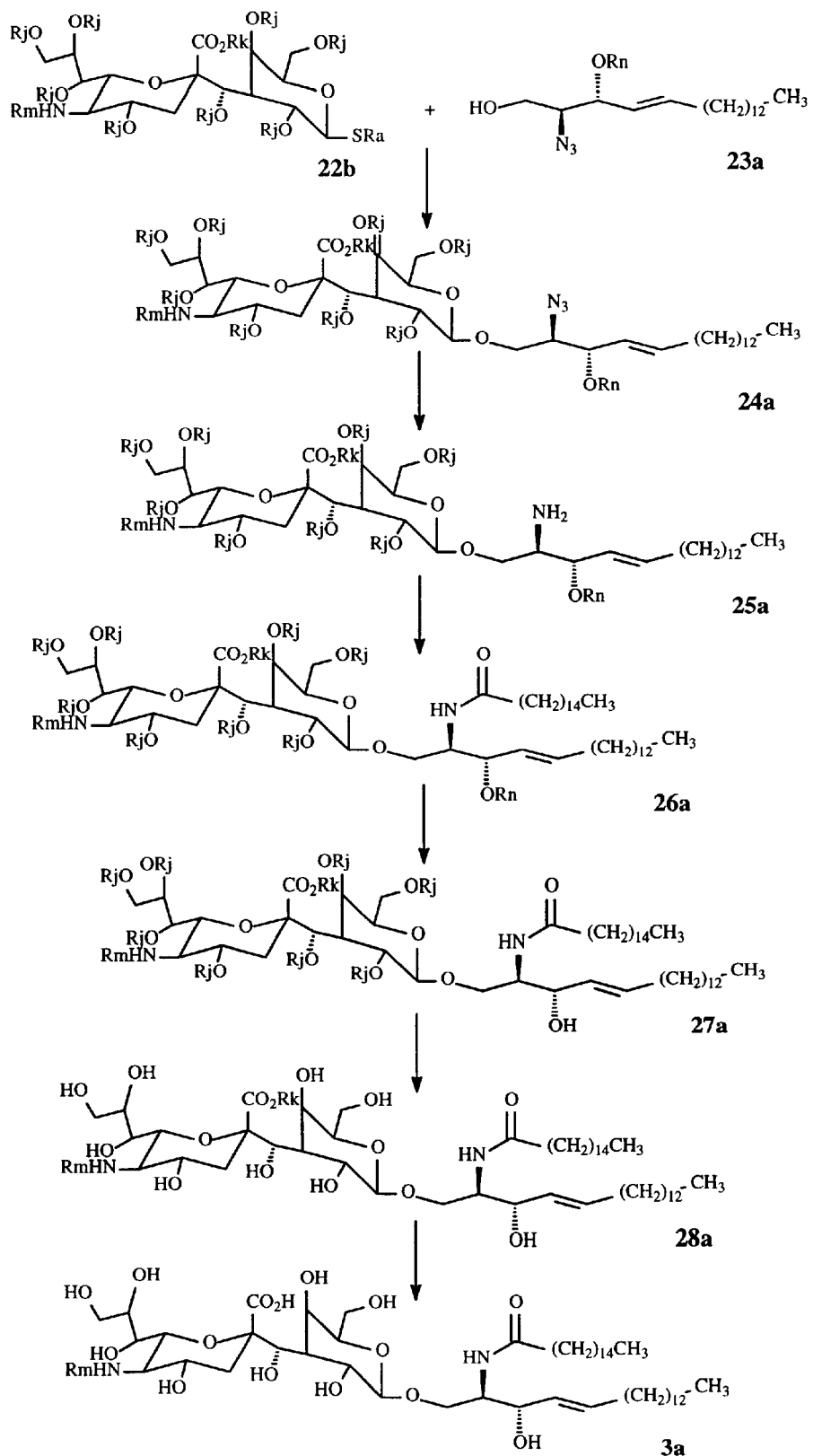
Figure 8:
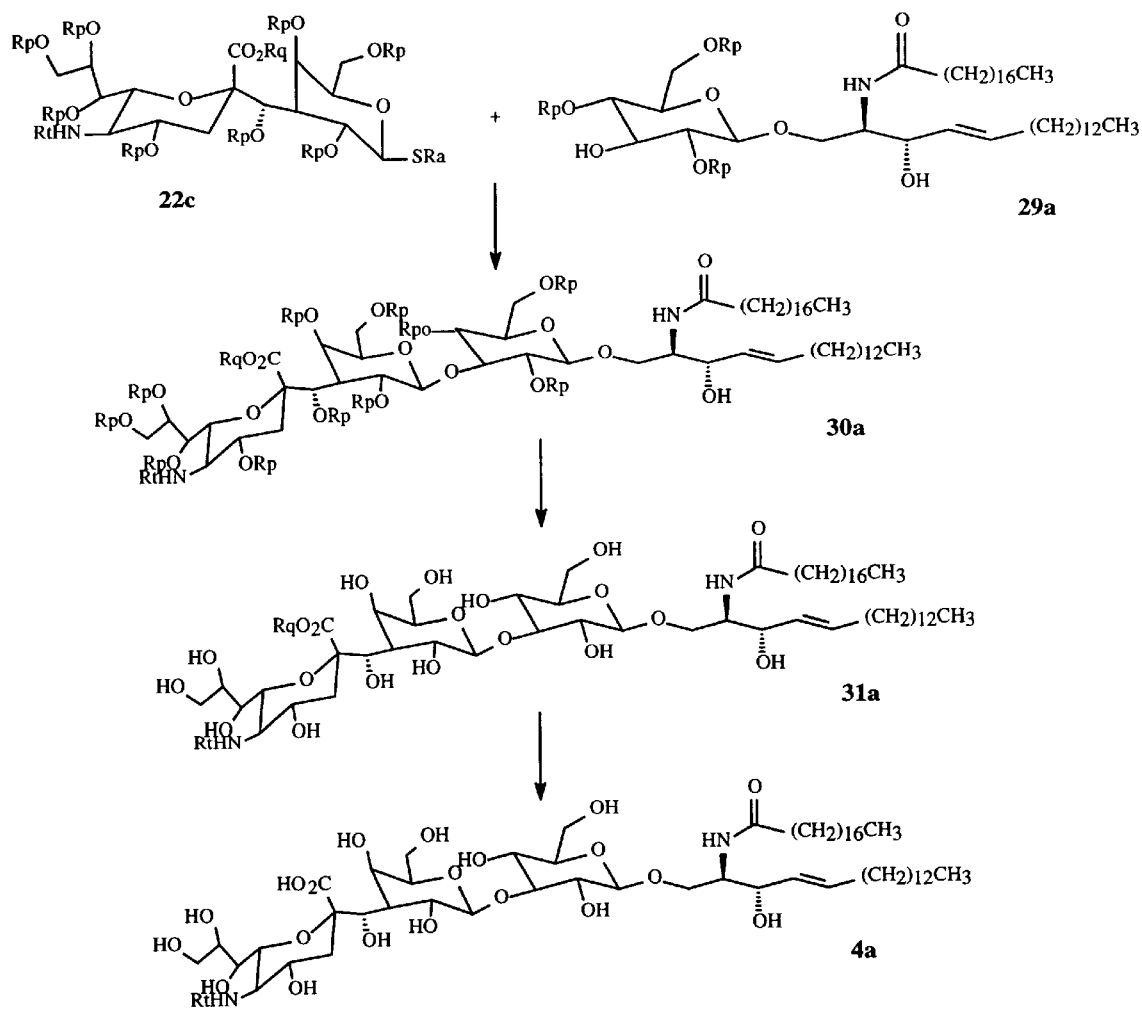

As illustrated in FIG. 6, a compound of formula 4 can be prepared by reacting a compound of formula 22 with a compound of formula 29 to give a compound of formula 30. The reaction can be carried out in any suitable solvent or combination of solvents. For example, the reaction can conveniently be carried out in dichloromethane in the presence of a stoichiometric amount of dimethyl(methylthio)sulfonium triflate (DMTST) or a similar activating reagent. Compound 30 can be deacylated to give a compound of formula 31. The reaction can conveniently be carried out with sodium methoxide in methanol. Conversion of the ester 31 to a compound of formula 4 can be carried out under standard conditions, for example, with aqueous potassium hydroxide.

Compounds of formula I wherein $R_2$ is hydrogen can conveniently be prepared from a suitably protected corresponding compound of formula I wherein $R_2$ is hydroxy by removal of the hydroxy using a procedure similar to that described by Barton D. H. R., et al., *J. C. S. Perkin I*, 1975, 1574–1585 followed by deprotection to yield a compound of formula I. For example, C-disaccharide (18a) with 1,1'-thiocarbonyldiimidazole in dry dichloromethane gave the corresponding thiocarbonate, which was deoxygenated using tributyltin hydride and 2,2-azobis(2-methylpropionitrile) (AIBN) in toluene to give the corresponding compound of formula I wherein $R_2$ is hydrogen. The starting compound 29 can be prepared from glucose and the requsite ceramic acid or azido sphinosine using standard methods.

The invention provides a method for preparing a compound of formula 21 comprising acylating compound 19.

The invention provides a method for preparing a compound of formula 19 comprising hydrogenating compound of formula 18.

The invention provides a method for preparing a compound of formula 18 comprising reacting an aldehyde of formula 15 with a phenylsulfone of formula 17 in the presence of a lanthanide metal (e.g. $SmI_2$).

The invention provides a method for preparing a compound of formula 21a comprising protecting the hydroxy groups of a corresponding compound of formula 19a.

The invention provides a method for preparing a compound of formula 19a comprising deprotecting a corresponding compound of formula 18a herein each Rh is independently a hydroxy protecting group that can be selectively removed in the presence of Rc and each Re.

The invention provides a method for preparing a compound of formula 18a comprising reacting an aldehyde of formula 15a with the requsite compound of formula 17a wherein Rk is arylsulfonyl or heteroarylsulfonyl; in the presence of a lanthanide metal.

The invention provides a method for preparing a compound of formula 28 (FIG. 5) comprising removing the acyl (Ac) protecting groups from a compound of formula 27 to provide the compound of formula 28.

The invention provides a method for preparing a compound of formula 27 comprising desilylating a compound of formula 26 to provide the compound of formula 27.

The invention provides a method for preparing a compound of formula 26 comprising acylating the amine of formula 25 to give the compound of formula 26.

The invention provides a method for preparing a compound of formula 25 comprising reducing the azido group in a compound of formula 24 to give the compound of formula 25.

The invention provides a method for preparing a compound of formula 24 comprising reacting a compound of formula 22 with an azidosphingosine of formula 23 to give the compound of formula 24.

The invention provides a method for preparing a compound of formula 31 comprising removing the acyl (Ac) protecting groups from a compound of formula 30 to provide the compound of formula 31.

The invention provides a method for preparing a compound of formula 30 comprising reacting a compound of formula 22 with a compound of formula 29 to provide the compound of formula 30.

The invention provides a method for preparing a compound of formula 28a comprising removing the $R_j$ protecting groups from a compound of formula 27a wherein each $R_j$ is independently a suitable hydroxy protecting group, to provide the compound of formula 28a.

The invention provides a method for preparing a compound of formula 27a comprising removing the $R_n$ protecting group from a compound of formula 26a wherein $R_n$ is a suitable hydroxy protecting group that can be removed in the presence of $R_j$, $R_k$, and $R_m$ to provide the compound of formula 27a.

The invention provides a method for preparing a compound of formula 26a comprising acylating an amine of formula 25a to give the compound of formula 26a.

The invention provides a method for preparing a compound of formula 25a comprising reducing the azido group in a compound of formula 24a to give the compound of formula 25a.

The invention provides a method for preparing a compound of formula 24a comprising reacting a compound of formula 22b, wherein $R_a$ is aryl, optionally substituted with 1, 2, 3, or 4 substituents independently selected from the group consisting of halo, nitro, cyano, trifluoromethoxy, $(C_1-C_6)$alkyl, $(C_1-C_6)$alkoxy, $(C_1-C_6)$alkanoyl, halo$(C_1-C_6)$alkyl, hydroxy$(C_1-C_6)$alkyl, $(C_1-C_6)$alkoxycarbonyl, $(C_1-C_6)$alkylthio, and $(C_1-C_6)$alkanoyloxy, with an azidosphingosine of formula 23a wherein $R_n$ is a suitable hydroxy protecting group, to give the compound of formula 24a.

The invention provides a method for preparing a compound of formula 31a comprising removing the $R_p$ protecting groups from a compound of formula 30a wherein each $R_p$ is independently a suitable hydroxy protecting group to provide the compound of formula 31a.

The invention provides a method for preparing a compound of formula 30a comprising reacting a compound of formula 22c, wherein $R_a$ is aryl, optionally substituted with 1, 2, 3, or 4 substituents independently selected from the group consisting of halo, nitro, cyano, trifluoromethoxy, $(C_1-C_6)$alkyl, $(C_1-C_6)$alkoxy, $(C_1-C_6)$alkanoyl, halo$(C_1-C_6)$alkyl, hydroxy$(C_1-C_6)$alkyl, $(C_1-C_6)$alkoxycarbonyl, $(C_1-C_6)$alkylthio, and $(C_1-C_6)$alkanoyloxy, with a compound of formula 29a to provide the compound of formula 30a.

The invention also provides a composition of matter comprising a peptide or protein linked to a C-glycoside component of formula II:

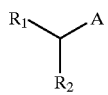

(II)

wherein: $R_1$ is the residue of a sialic acid; $R_2$ is hydrogen, hydroxy, or $(C_1-C_6)$alkanoyloxy; and A is the residue of a monosaccharide.

The term "amino acid," comprises the residues of the natural amino acids (e.g. Ala, Arg, Asn, Asp, Cys, Glu, Gln, Gly, His, Hyl, Hyp, Ile, Leu, Lys, Met, Phe, Pro, Ser, Thr, Trp, Tyr, and Val) in D or L form, as well as unnatural amino acids (e.g. phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine, ornithine, citruline, -methyl-alanine, para-benzoylphenylalanine, phenylglycine, propargylglycine, sarcosine, and tert-butylglycine). The term also comprises natural and unnatural amino acids bearing a conventional amino protecting group (e.g. acetyl or benzyloxycarbonyl), as well as natural and unnatural amino acids protected at the carboxy terminus (e.g. as a $(C_1-C_6)$alkyl, phenyl or benzyl ester or amide). Other suitable amino and carboxy protecting groups are known to those skilled in the art (See for example, T. W. Greene, *Protecting Groups In Organic Synthesis;* Wiley: New York, 1981, and references cited therein).

The term "peptide" describes a sequence of 1 to 10 amino acids (e.g. as defined hereinabove). The sequence may be linear or cyclic. For example, a cyclic peptide can be prepared or may result from the formation of disulfide bridges between two cysteine residues in a sequence. A peptide can be linked to a C-glycoside component of formula II through the carboxy terminus, the amino terminus, or through any other convenient point of attachment, such as, for example, through the oxygen of a serine. Preferably a peptide comprises 2 to 10 amino acids Peptide derivatives can be prepared as disclosed in U.S. Pat. No. 4,612,302; 4,853,371; and 4,684,620.

The term "protein" describes a poly peptide of more than 10 amino acids. A peptide can be linked to a C-glycoside component of formula II through the carboxy terminus, the amino terminus, or through any other convenient point of attachment, such as, for example, through the oxygen of a serine. A variety of proteins (e.g. mucin, S. Aduri, et al., *Cancer Immunol. Immunother.,* 1995, 41, 185–192) contain carbohydrates linked to the oxygen of a serine or threonine residue. Such a protein, or a fragment or portion of such a protein, containing 1 or more (e.g. 1 to 5) serine residues can glycosylated to obtain a C-glycoside glyco-protein having improved physical or pharmacoogical propeties.

A specific protein that can be linked to a C-glycoside component of formula II, to form a C-glycoside linked protein of the invention, is mucin. Additionally, a C-glycoside linked protein or peptide of the invention can be prepared by linking a biologically active fragment or portion of the protein mucin to a C-glycoside component of formula II. A C-glycoside linked protein or peptide of the invention can also be prepared by linking a C-glycoside component of formula II to an sTn analog (e.g. an sTn analog disclosed by Ikeda K., et al., *J. synth. Org. Chem.* (Japan), 1998, 56, 567–580).

In a composition of matter of the invention $R_1$ can specifically be a residue of neuraminic acid, 3-deoxy-D-glycero-D-galacto-2-nonulosonic acid, or 3-deoxy-D-manno-2-octulosonic acid.

In a composition of matter of the invention $R_1$ can specifically be ethyl-5-acetanido-4,7,8,9-tetra-O-acetyl-3,5-dideoxy-D-glycero-α-D-galacto-non-2-ulopyranosyl)onate.

In a composition of matter of the invention A can specifically be a glucose or galactose residue.

In a composition of matter of the invention A can specifically be phenyl 2,4,6-tri-O-acetyl-3-deoxy-thio-β-D-galacto-pyranosid-3-yl.

In a composition of matter of the invention the protein can specifically be mucin.

In a composition of matter of the invention the peptide or protein can specifically be a biologically active fragment or portion of the protein mucin.

In a composition of matter of the invention the peptide or protein can specifically be a sTn analog.

The invention will now be illustrated by the following non-limiting Examples, wherein the following general procedures were utilized, unless otherwise stated. Nuclear magnetic resonance ($^1$H NMR) spectra were recorded at 25° C., in deuterated chloroform or methanol. Chemical shifts were recorded in ppm ($\delta$) and coupling constants in Hz, relative to tetramethylsilane as internal standard. The $^1$H NMR spectra were fully assigned using single frequency decoupling, 2D COSY, and 2D NOESY NMR spectroscopy. Melting points are uncorrected. Thin-layer chromatography (TLC) was performed using E. Merck plates of Silica Gel 60 with fluorescent indicator. Visualization was effected by spraying plates with Von's reagent (1.0 g ceric ammonium sulfate and 24.1 g ammonium molybdate in 31 mL sulfuric acid and 470 mL water) followed by heating at 140° C. Flash chromatography was conducted with silica gel (230–430 mesh, E. Merck).

EXAMPLES

Example 1

Methyl 5-acetamido-4,7,8,9-tetra-O-acetyl-2,6-anhydro-3,5-dideoxy-2-C-{(R)-hydroxy-[3-(p-methoxyphenyl 2,4,6-tri-O-benzyl-3-deoxy-β-D-galactopyranosidyl)]-methyl}-D-erythro-L-manno-nonate 18(R) and methyl 5-acetamaido-4,7,8,9-tetra-O-acetyl-2,6-anhydro-3,5-dideoxy-2-C-{(R)-hydroxy-[3-(p-methoxyphenyl 2,4,6-tri-O-benzyl-3-deoxy-β-D-galactopyranosidyl)]-methyl}-D-erythro-L-manno-nonate 18(S)

A solution of compounds 15 (111 mg, 0.19 mmol) and 17 (100 mg, 0.16 mmol) in CHCl$_3$ (2 mL) was evaporated to dryness and the resulting residue dried for 1 hour under high vacuum. To the dried residue placed under nitrogen was added a solution of freshly prepared SmI$_2$ (~0.1 M in tetrahydrofuran, 15 mL), and the reaction mixture stirred at room temperature for 15 minutes The reaction mixture was then diluted with ether, washed successively with 1N HCl, satd aq Na$_2$S$_2$O$_3$ and H$_2$O, dried over anhydrous Na$_2$SO$_4$, filtered and the solvents were evaporated. The residue was purified by chromatography on silica gel (CHCl$_3$—CH$_3$OH, v/v 40:1) to give 18(R) and 18(S) as a white solid in 85% yield (142 mg). 18(R); $^1$H NMR (500 MHz, CDCl$_3$): δ1.77 (t, 1H, J$_{3a,4}$, J$_{3a,3e}$ 12.4 Hz, H-3a), 1.89, 1.96, 2.00, 2.02 and 2.17 (5 s, 3H each, 5 OAc), 2.15 (ovl with OAc, 1H, H-3'), 2.54 (dd, 1H, J$_{3e,4}$ 4.4 Hz, H-3e), 3.68 (dd, 1H, J$_{5',6'b}$ 6.7 Hz, J$_{6'a,6'b}$ 9.3 Hz, H-6'b), 3.73 (s, 3H, CO$_2$CH$_3$), 3.77 (s, 3H, PhOCH$_3$), 3.79 (dd, 1H, J$_{5',6'a}$<1.5 Hz, H-6'a), 3.90 (t, 1H, H-5'), 3.97 (dd, 1H, J$_{4,5}$, J$_{5,6}$ 10.4 Hz, J$_{5,NH}$ 10.2 Hz, H-5), 4.00 (m ovl with H-9b, 1H, J$_{1',2'}$ 7.5 Hz, H-2'), 4.01 (dd ovl with H-2', 1H, J$_{9a,9b}$ 12.5 Hz, H-9b), 4.11 (m, 2H, H-6 and Hb), 4.23 (dd, 1H, J$_{8,9a}$ 2.2 Hz, H-9a), 4.35 (bs, 1H, H-4'), 4.52, 4.58, 4.61, 4.67, 4.76 and 5.06 (6 d, 1H each, 3CH$_2$Ph), 4.80 (m, 1H, H-4), 5.01 (d, 1H, H-1'), 5.14 (d, 1H, NH), 5.28 (dd, 1H, J$_{6,7}$<1.5 Hz, J$_{7,8}$ 9.4 Hz, H-7), 5.44 (m, 1H, H-8), 6.60 and 7.10 (2d, 2H each, PhOCH$_3$), 7.20–7.40 (m, 15H, 3CH$_2$Ph). 18(S); $^1$H NMR (500 MHz, CDCl$_3$): 71.82, 1.84, 1.94, 2.00 and 2.16 (5 s, 3H each, 5 OAc), 2.21 (dd, 1H, J$_{3e,4}$ 5.1 Hz, H-3e), 2.27 (t, 1H, J$_{3a,4}$, J$_{3a,3e}$ 13.0 Hz, H-3a), 2.38 (m, 1H, J$_{2',3'}$ 11.2 Hz, H-3'), 3.17 (d, 1H, J$_{Hb,OH}$ 1.5 Hz, OH), 3.64 (m, 2H, Hb and H-5'), 3.73 (m, 1H, J$_{5',6'b}$ 2.9 Hz, H-6'b), 3.76 (s, 3H, CO$_2$CH$_3$), 3.77 (s, 3H, PhOCH$_3$), 3.82 (m, 2H, J$_{8,9b}$ 5.0 Hz, H-9b and H-6'a), 3.90 (m, 2H, H-5 and H-4'), 3.93 (dd, 1H, J$_{5,6}$ 10.4 Hz, J$_{6,7}$ 2.0 Hz, H-6), 4.07 (dd, 1H, J$_{1',2'}$ 7.4 Hz, H-2'), 4.14 (dd, 1H, J$_{8,9a}$ 1.5 Hz, J$_{9a,9b}$ 12.0 Hz, H-9a), 4.47, 4.48, 4.54, 4.62, 4.66 and 5.18 (6 d, 1H each, 3CH$_2$Ph), 4.76 (m, 1H, H-4), 5.02 (d, 1H, J$_{5,NH}$ 9.7 Hz, NH), 5.20 (dd, 1H, J$_{7,8}$ 8.9 Hz, H-7), 5.29 (d, 1H, H-1'), 5.43 (m, 1H, H-8), 6.80 and 7.00 (2d, 2H each, PhOCH$_3$), 7.20–7.40 (m, 15H, 3CH$_2$Ph).

The intermediate compound 15 was prepared as follows, a. p-Methoxyphenyl 2,3,4,6-tetra-O-acetyl-β-D-galactopyranoside (6)

p-methoxyphenol (20.5 mmol, 2.5 g) and trimethylsilyl trifluoromethanesulfonate (0.25 mL) were added to a solution of β-D-galactose pentaacetate (5.0 g, 12.8 mmol) in anhydrous CH$_2$Cl$_2$ at 0° C. under nitrogen. After 4 hours at 0° C., the reaction mixture was neutralized by addition of triethylamine (1 mL) and concentrated under reduced pressure. Purification by chromatography on silica gel (ethyl acetate-petroleum ether, v/v 1:3→1.5:1) afforded 6 as an amorphous white solid in 92% yield (5.35 g). Litt[22] [α$_D$]=+9.6° (c 0.54, CHCl$_3$); [α$_D$]$^{23}$=+3° (c 1, CHCl$_3$); $^1$H NMR (500 MHz, CDCl$_3$): δ2.01, 2.06, 2.08 and 2.19 (4 s, 3H each, 4 OAc), 3.78 (s, 3H, OMe), 4.01 (m, 1H, H-5), 4.16 (dd, 1H, J$_{5,6b}$ 6.5 Hz, J$_{6a,6b}$ 11.3 Hz, H-6b), 4.23 (dd, 1H, J$_{5,6a}$ 6.9 Hz, H-6a), 4.92 (d, 1H, J$_{1,2}$ 8.0 Hz, H-1), 5.09 (dd, 1H, J$_{2,3}$ 10.4 Hz, J$_{3,4}$ 3.3 Hz, H-3), 5.5.44–5.48 (m, 2H, H-2 and H-4), 6.80 and 6.96 (2 d, 2H each, Ph).

b. p-Methoxyphenyl 3-O-allyl-β-D-galactopyranoside (8)

To a solution of 6 (5.25 g, 11.57 mmol) in anhydrous methanol (50 mL) and under nitrogen was added a catalytic amount of sodium methoxide. After 5 hours at room temperature, the reaction mixture was neutralized with resin IR 120 (H$^+$), filtered, and the solvent was evaporated. The resulting p-methoxyphenyl β-D-galactopyranoside 7 was used without any further purification and characterization. Compound 7 (3.24 g, 11.34 mmol) in solution in anhydrous methanol (50 mL) and under nitrogen was reacted with dibutyltin oxide (3.11 g, 12.48 mmol). After 4 hours at reflux, the reaction mixture was concentrated under vacuum. The dried residue was suspended in toluene (80 mL) and treated with allyl bromide (1.17 mL, 13.61 mmol) and tetrabutylammonium iodide (4.17 g, 11.34 mmol). The suspension was stirred under nitrogen at 60° C. for 18 h. TLC of the resulting brownish solution showed the presence of 50% of unreacted starting material. This solution was reacted with additional allyl bromide (0.58 mL, 6.80 mmol). After 18 hours at 60° C., the solvent was evaporated and the residue was purified by chromatography on silica gel (ethyl acetate) to afford 8 in 85% yield (3.16 g), isolated as yellowish crystals. Recrystallization of 8 in ethyl acetate afforded white crystals. mp=140–141° C.; [α$_D$]$^{23}$ =–8° (c 1, CHCl$_3$); $^1$H NMR (500 MHz, CD$_3$OD): δ3.32 (m, 1H, H-5), 3.39 (dd, 1H, J$_{2,3}$ 9.5 Hz, J$_{3,4}$ 3.2 Hz, H-3), 3.58 (t, 1H, J$_{5,6b}$ 6.1 Hz, J$_{6a,6b}$ 6.0 Hz, H-6b), 3.75 (s, 3H, OMe), 3.78 (dd, 1H, J$_{5,6a}$ 4.8 Hz, H-6a), 3.86 (dd, 1H, J$_{1,2}$ 7.9 Hz, H-2), 4.07 (d, 1H, J$_{4,5}$<1.5 Hz, H-4), 4.17 and 4.26 (2 dd, 1H each, OCH$_2$), 4.74 (d, 1H, H-1), 5.18 and 5.34 (2 dd, 1H each, CH=CH$_2$), 6.00 (m, 1H, CH=CH$_2$), 6.80 and 7.08 (2 d, 2H each, Ph). Anal. Calcd for C$_{16}$H$_{22}$O$_7$ (326.3): C 58.89, H 6.79; found: C 58.37, H 6.91.

c. p-Methoxyphenyl 3-O-allyl-2,4,6-tri-O-benzyl-β-D-galactopyranoside (9)

To a solution of compound 8 (1.21 g, 3.71 mmol) in anhydrous DMF (15 mL), under nitrogen and cooled at 0° C., was added NaH (116 mg, 4.83 mmol). The reaction mixture was stirred 15 minutes at 0° C. and treated with benzyl bromide (0.66 mL, 5.57 mmol). After 12 hours at room temperature, the reaction mixture was cooled at 0° C., quenched by slow addition of water and extracted with chloroform. The combined organic layers were washed with H$_2$O, dried over anhydrous Na$_2$SO$_4$, filtered and the solvents were evaporated. Purification by chromatography on silica gel (ethyl acetate-petroleum ether, v/v 1:3) afforded 91% as white crystals in 91% yield (2.01 g). mp=59–61° C.; [α$_D$]$^{24}$=–23° (c 1, CHCl$_3$); $^1$H NMR (500 MHz, CDCl$_3$): δ3.48 (dd, 1H, J$_{2,3}$ 9.6 Hz, J$_{3,4}$ 2.8 Hz, H-3), 3.63 (bs, 3H, H-5, H-6a and H-6b), 3.75 (s, 3H, OMe), 3.90 (d, 1H, J$_{4,5}$<1.5 Hz, H-4), 4.01 (dd, 1H, J$_{1,2}$ 7.8 Hz, H-2), 4.22 (m, 2H, OCH$_2$), 4.40, 4.45, 4.64, 4.84, 4.96 and 4.97 (6 d, 1H each, J$_{A,B}$ 11.7 Hz, CH$_2$Ph), 4.83 (d, 1H, H-1), 5.19 and 5.33 (2 dd, 1H each, CH=CH$_2$), 5.95 (m, 1H, CH=CH$_2$), 6.78 and 7.02 (2 d, 2H each, C$_6$H4), 7.22–7.40 (m, 15H, 3C$_6$H$_5$). Anal. Calcd for C$_{37}$H$_{40}$O$_7$ (596.7): C 74.48, H 6.76; found: C 74.32, H 6.75.

d. p-Methoxyphenyl 2,4,6-tri-O-benzyl-β-D-galactopyranoside (10)

Compound 9 (2.67 g, 4.49 mmol) was dissolved in a mixture of anhydrous methanol and toluene (21 mL, v/v 3:1) and reacted with PdCl$_2$ (~100 mg) under nitrogen and at room temperature. After 4 hours of reaction, the reaction mixture was filtrated over a pad of Celite and the solvents were evaporated. Purification of the residue by chromatography on silica gel (ethyl acetate-petroleum ether, v/v 1:4) afforded 10 as white crystals in 94% yield (2.35 g). mp=84–86° C.; [α$_D$]$^{24}$=–11° (c 1, CHCl$_3$); $^1$H NMR (500 MHz, CDCl$_3$): δ3.66–3.73 (m, 3H, H-5, H-6a and H-6b), 3.74 (t, 1H, J$_{2,3}$ 9.5 Hz, J$_{3,4}$ 2.9 Hz, H-3), 3.76 (s, 3H, OMe), 3.83 (dd, 1H, J$_{1,2}$ 7.7 Hz, H-2), 3.90 (d, 1H, J$_{4,5}$<1.5 Hz, H-4), 4.44, 4.49, 4.66, 4.78, 4.81 and 5.05 (6 d, 1H each, J$_{A,B}$ 11.8 Hz, CH$_2$Ph), 4.84 (d, 1H, H-1), 6.78 and 7.02 (2 d, 2H each, C$_6$H$_4$), 7.22–7.40 (m, 15H, 3C$_6$H$_5$). Anal. Calcd for C$_{34}$H$_{36}$O$_7$ (556.7): C 73.36, H 6.52; found: C 72.96, H 6.63.

e. p-Methoxyphenyl 2,4,6-tri-O-benzyl-β-D-xylo-hex-3-ulopyranoside (11)

Compound 10 (2.93 g, 5.27 mmol) in solution in anhydrous DMSO (18 mL) was reacted with Ac$_2$O (15 mL) under nitrogen and at room temperature. After 12 h, Ac$_2$O was evaporated and the remaining solution diluted with H$_2$O and extracted with CHCl$_3$. The combined organic layers were washed with H$_2$O, dried over anhydrous Na$_2$SO$_4$, filtered and the solvent was evaporated. The residue was purified by chromatography on silica gel (ethyl acetate-petroleum ether, v/v 1:3) to give 11 as a light yellow solid in 84% yield (2.45 g). mp=85–87° C.; [α$_D$]$^{23}$=–52° (c 1, CHCCl$_3$); $^1$H NMR (500 MHz, CDCl$_3$): δ3.76 (s, 3H, OMe), 3.66–3.73 (bs, 3H, H-5, H-6a and H-6b), 3.92 (s, 1H, J$_{4,5}$<1.5 Hz, H-4), 4.34, 4.42, 4.45, 4.51, 4.59 and 4.94 (6 d, 1H each, J$_{A,B}$ 11.8 Hz, CH$_2$Ph), 4.76 (bd, 2H, H-1 and H-2), 6.78 and 7.08 (2 d, 2H each, C$_6$H$_4$), 7.22–7.40 (m, 15H, 3C$_6$H$_5$). Anal. Calcd for C$_{34}$H$_{34}$O$_7$ (554.6): C 73.63, H 6.18; found: C 73.76, H 6.35.

f. p-Methoxyphenyl 2,4,6-tri-O-benzyl-3-deoxy-3-C-(methylene)-β-D-xylo-hex-3-ulopyranoside (12)

To a solution of 11 (2.36 g, 4.26 mmol) in anhydrous THF (60 mL) under nitrogen and cooled at –40° C., was added dropwise within 20 minutes Tebbe's reagent (17 mL). After 1 hours at –40° C., the reaction mixture was allowed to warm at 0° C. After 50 minutes at 0° C. was added very slowly a 10% aq NaOH solution (10 mL), and the reaction mixture was stirred 30 minutes at 0° C. The reaction mixture was filtered through a pad of Celite and the solid washed several times with ethyl acetate. The combined organic extracts were evaporated and the residue purified by chromatography on silica gel (ethyl acetate-petroleum ether, v/v 1:5) to afford 12 as white crystals in 84% yield (1.98 g). mp=74–76° C.; [α$_D$]$^{23}$=–9° (c 1, CHCl$_3$); $^1$H NMR (500 MHz, CDCl$_3$): δ3.74–3.81 (m, 3H, H-5, H-6a and H-6b), 3.76 (s, 3H, OMe), 3.98 (s, 1H, J$_{4,5}$<1.5 Hz, H-4), 4.30 (dt, 1H, J$_{1,2}$ 7.6 Hz, H-2), 4.24, 4.48, 4.52, 4.54, 4.79 and 4.99 (6 d, 1H each, J$_{A,B}$ 11.7 Hz, CH$_2$Ph), 4.81 (d, 1H, H-1), 5.17 and 5.56 (2 t, 1H each, C=CH$_2$), 6.79 and 7.03 (2 d, 2H each, C$_6$H$_4$), 7.22–7.42 (m, 15H, 3C$_6$H$_5$). Anal. Calcd for C$_{35}$H$_{36}$O$_6$ (552.6): C 76.06, H 6.57; found: C 76.16, H 6.70.

g. p-Methoxyphenyl 2,4,6-tri-O-benzyl-3-deoxy-3-C-(hydroxymethyl)-β-D-galacto-hexopyranoside (13) and p-methoxyphenyl 2,4,6-tri-O-benzyl-3-deoxy-3-C-(hydroxymethyl)-β-D-gulo-hexopyranoside (14)

Compound 12 (1.89 g, 3.42 mmol) in solution in anhydrous ThF (80 mL) was reacted with 9-BBN (0.5 M in THF, 43 mL, 21.6 mmol) at reflux and under nitrogen. After 5 hours of reaction, the reaction mixture was cooled at 0° C. and a 10% aq solution of NaOH (34 mL) was slowly added followed by 30% aq solution of H$_2$O$_2$ (34 mL). The reaction mixture was stirred 30 minutes and extracted with CHCl$_3$. The combined organic extracts were washed with a 20% aq solution of sodium hydrogen sulfite and with H$_2$O, dried over anhydrous Na$_2$SO$_4$, filtered and the solvent were evaporated. The residue was purified by chromatography on silica gel (ethyl acetate-petroleum ether, v/v 1:5) to give 13 and 14 as a colorless oil in 91% yield (2.452 g), in a ratio 13:14=1.5:1.0. 13, $^1$H NMR (500 MHz, CDCl$_3$): δ1.90 (m, 1H, J$_{2,3}$ 11.1 Hz, J$_{3,4}$<1.5 Hz, H-3), 3.65–3.87 (m, 5H, H-5, H-6a, H-6b, CH$_2$), 3.77 (s, 3H, OMe), 3.85 (dd, 1H, J$_{1,2}$ 7.7 Hz, H-2), 3.95 (d, 1H, H-4), 4.35–5.03 (m, 3CH$_2$Ph), 4.92 (d, 1H, H-1), 6.80 and 7.04 (2 d, 2H each, C$_6$H$_4$), 7.20–7.40 (m, 15H, 3C$_6$H$_5$). 14, $^1$H NMR (500 MHz, CDCl$_3$): δ2.61 (bq, 1H, J$_{2,3}$ 5.5 Hz, J$_{3,4}$<1.5 Hz, H-3), 3.65–3.87 (m, 4H, H-6a, H-6b, CH$_2$), 3.76 (s, 3H, OMe), 3.95 (d, 1H, H-4), 4.02 (bt, 2H, H-2, H-5) 4.35–5.03 (m, 3 CH$_2$Ph), 5.27 (d, 1H, J$_{1,2}$ 6.2 Hz, H-1), 6.80 and 7.04 (2 d, 2H each, C$_6$H$_4$), 7.20–7.40 (m, 15H, 3C$_6$H$_5$).

h. p-Methoxyphenyl 2,4,6-tri-O-benzyl-3-deoxy-3-C-(formyl)-β-D-galacto-hexopyranoside (15) and p-methoxyphenyl 2,4,6-tri-O-benzyl-3-deoxy-3-C-(formyl)-β-D-gulo-hexopyranoside (16)

Anhydrous DMSO (1.30 µL) was carefully added to a 2.0 M solution of oxalyl chloride in CH$_2$Cl$_2$ (3.86 mL, 7.71 mmol) under nitrogen and cooled at –78° C. After 10 minutes a solution of 12-13 (1.76 g, 3.08 mmol) in anhydrous CH$_2$Cl$_2$ (10 mL) was added dropwise and the reaction mixture stirred 1 hours at –78° C. The reaction mixture was treated with triethylamine (4.3 mL, 30.9 mmol) for 45 minutes at –78° C., and allowed to warrn at 0° C., quenched by addition of $H_2O$ and extracted with $CHCl_3$. The combined organic layers were washed with satd aq $NaHCO_3$ and $H_2O$, dried over anhydrous $Na_2SO_4$, filtered and the solvents were evaporated. The residue was purified by chromatography on silica gel (ethyl acetate-petroleum ether, v/v 1:5) to give 16 as a colorless oil in 13% yield (0.22 g) and 15 as white needles in 60% yield (1.05 g). 16 $[\alpha_D]^{23}$=−32° (c 0.5, $CHCl_3$); $^1$H NMR (500 MHz, $CDCl_3$): δ2.56 (bd, 1H, $J_{1,2}$ 7.2 Hz, $J_{2,3}$ 6.6 Hz, H-3), 3.67 (m, 2H, H-6a and H-6b), 4.05 (m, 1H, H-5), 3.76 (s, 3H, OMe), 4.07 (m, 1H, H-4), 5.16 (dd, 1H, H-2), 4.41, 4.45, 4.47, 4.48, 4.71 and 4.95 (6d, 1H each, $J_{A,B}$ 11.7Hz,$CH_2$Ph), 5.10 (d, 1H, H-1), 6.78 and 7.00 (2 d, 2H each, $C_6H_4$), 7.20–7.38 (m, 15H, $3C_6H_5$), 9.89 (s, 1H, CHO). Anal. Calcd for $C_{35}H_{36}O_7$ (568.7): C 73.92, H 6.38; found C 72.98, H 7.08. 15 mp=114–116° C.; $[\alpha_D]^{23}$=+1° (c 1, $CHCl_3$); $^1$H NMR (500 MHz, $CDCl_3$): δ2.56 (bd, 1H, $J_{1,2}$ 7.7 Hz, $J_{2,3}$ 11.1 Hz. H-3), 3.64 (dd, 1H, $J_{5,6b}$ 9.3 Hz, $J_{6a,6b}$ 9.3 Hz, H-6b), 3.69 (t, 1H, H-6a), 3.76 (m, 1H, H-5), 3.76 (s, 3H, OMe), 4.22 (d, 1H, $J_{4,5}$<1.5 Hz, H-4), 4.34 (dd, 1H, H-2), 4.47, 4.48, 4.49, 4.52, 4.82 and 5.05 (6 d, 1H each, $J_{A,B}$ 11.7 Hz, $CH_2$Ph), 4.94 (d, 1H, H-1), 6.80 and 7.08 (2 d, 2H each, $C_6H_4$), 7.20–7.38 (m, 15H, $3C_6H_5$), 9.55 (s, 1H, CHO). Anal. Calcd for $C_{35}H_{36}O_7$ (568.7): C 73.92, H 6.38; found C 73.39, H 6.36.

The intermediate sulfone 17 was prepared using a procedure similar to that described by Cao, S., et al., *Tetrahedron Asymetry*, 1994, 5, 2303–2312 and Marra, A., and Sinay, P., *Carbohydrate Research*, 1989, 187, 35–42.

Example 2

Methyl 5-acetamido-4,7,8,9-tetra-O-acetyl-2,6-anhydro-3,5-dideoxy-2-C-{(R)-hydroxy-[3-p-methoxyphenyl 3-deoxy-β-D-galactopyranosidyl)]-methyl}-D-erythro-L-manno-nonate 19(R) and methyl 5-acetaniido-4,7,8,9-tetra-O-acetyl-2,6-anhydro-3,5-dideoxy-2-C-{(R)-hydroxy-[3-(p-methoxy-phenyl 3-deoxy-β-D-galactopyranosidyl)]-methyl}-D-erythro-L-manno-nonate 19(S)

A solution of compounds 18(R)–96818(S) (558 mg, 0.53 mmol) in EtOAc:$CH_3OH$:$H_2O$:80% aq AcOH (20 mL:20:mL:10 mL:1 drop) was stirred at room temperature under an atmosphere of $H_2$. After 15 hours, the reaction mixture was filtered over a pad of Celite and the filtrate evaporated under vacuum. The residue was purified by chromatography on silica gel ($CHCl_3$—$CH_3OH$, v/v 35:1) to give 19(R) and 19(S) as white solids in 54% (223 mg) and 36% (149 mg) respectively. 19(R); mp=146–149° C.; $[\alpha_D]^{23}$=+4' (c 1, $CHCl_3$); HRFABMS (+ve): Calcd for $C_{34}H_{47}NO_{19}$ $[M+Na]^+$ 796.2640; Found 796.2628; $^1$H NMR (500 MHz, $CDCl_3$): δ1.88, 2.01, 2.02, 2.15 and 2.17 (5 s, 3H each, 5 OAc), 1.86 (t, 1H, $J_{3a,4}$, $J_{3a,3e}$ 13.0 Hz, H-3a), 1.99 (ovl with OAc, 1H, H-3'), 2.54 (dd, 1H, $J_{3e,4}$ 4.4 Hz, H-3e), 3.63 (t, 1H, $J_{5',6'b}$ 5.5 Hz, $J_{6'a,6'b}$ 10.7 Hz, H-6'b), 3.77 (s, 6H, PhOCH$_3$ and CO$_2$CH$_3$), 3.83 (dd, 1H, $J_{5',6a}$<1.5 Hz, H-6'a), 3.89 (m, 1H, H-5'), 3.94 (dd, 1H, $J_{8,9b}$ 8.1 Hz, $J_{9a,9b}$ 12.3 Hz, H-9b), 4.08 (dd, 1H, $J_{4,5}$, $J_{5,6}$ 10.2 Hz, $J_{5,NH}$ 9.5 Hz, H-5), 4.22 (bt, 1H, $J_{1',2'}$ 7.6 Hz, $J_{2',3'}$ 9.4 Hz, H-2'), 4.30 (bd ovl with H-9a, 1H, $J_{6,7}$ 2.0 Hz, H-6), 4.33 (dd, 1H, $J_{8a,9a}$<1.5 Hz, H-9a), 4.37 and 4.75 (2 bs, 1H each, Hb and H-4'), 4.79 (m, 1H, H-4), 4.85 (d, 1H, H-1'), 5.22 (dd, 1H, $J_{7,8}$ 9.2 Hz, H-7), 5.28 (bd, 1H, NH), 5.56 (bt, 1H, H-8), 6.80 and 7.10 (2 d, 2H each, PhOCH$_3$). 19(S); mp=138–141° C.; $[\alpha_D]^{23}$=−12.5° (c 1, $CHCl_3$); HRFABMS (+ve): Calcd for $C_{34}H_{47}NO_{19}$ $[M+Na]^+$ 796.2640; Found 796.2629. $^1$H NMR (500 MHz, $CDCl_3$): δ1.86, 1.88, 2.04, 2.12 and 2.15 (5 s, 3H each, 5 OAc), 2.16 (bd ovl with OAc, 1H, H-3'), 2.31 (t, 1H, $J_{3a,4}$ 12.6 Hz, $J_{3a,3e}$ 13.1 Hz, H-3a), 2.46 (dd, 1H, $J_{3e,4}$ 4.6 Hz, H-3e), 3.66 (bt, 1H, H-6'b), 3.85 (bs, 2H, H-5' and H-6'a), 3.94 (dd, 1H, $J_{8,9b}$ 7.1 Hz, $J_{9a,9b}$ 12.0 Hz, H-9b), 3.95 (dd, 1H, $J_{5,6}$ 10.5 Hz, $J_{6,7}$ 1.9 Hz, H-6), 4.03 (dd, 1H, $J_{4,5}$ 10.5 Hz, $J_{5,NH}$ 10.0 Hz, H-5), 4.14 (bt, 1H, $J_{1',2'}$ 7.7 Hz, H-2'), 4.28 (bs, 2H, Hb and H-4'), 4.29 (dd, 1H, $J_{8,9a}$ 2.5 Hz, H-9a), 4.92 (m, 1H, H-4), 5.03 (d, 1H, H-1'), 5.21 (dd, 1H, $J_{7,8}$ 8.8 Hz, H-7), 5.02 (b, 1H, NH), 5.51 (m, 1H, H-8), 6.80 and 7.00 (2d, 2H each, PhOCH$_3$).

Example 3

Methyl 5-acetanido-4,7,8,9-tetra-O-acetyl-2,6-anhydro-3,5-dideoxy-2-C-{(R)-hydroxy-[3-(p-methoxyphenyl 2,4,6-tri-O-acetyl-3-deoxy-β-D-galactopyranosidyl)]-methyl}-D-erythro-L-manno-nonate 20(R)

A solution of 19(R) (52 mg, 0.067 mmol) in anhydrous pyridine (5 mL) was reacted with $Ac_2O$ (0.1 mL) under nitrogen. After 48 hours at room temperature, the reaction mixture was quenched with $CH_3OH$ and evaporated under vacuum. The residue was dried by coevaporation with toluene and purified by chromatography on silica gel ($CHCl_3$—$CH_3OH$, v/v 45:1) to afford 20(R) as a white solid in quantitative yield (60 mg). mp=120–122° C.; $[\alpha_D]^{23}$=+12° (c 1, $CHCl_3$); Anal. Calcd for $C_{40}H_{53}NO_{22}$ (899.9): C 53.39, H 5.94; found C 53.13, H 6.11. $^1$H NMR (500 MHz, $CDCl_3$): δ1.83 (t, 1H, $J_{3a,4}$ 12.2 Hz, $J_{3a,3e}$ 12.7 Hz, H-3a) 1.90, 2.02, 2.04, 2.06, 2.10, 2.11, 2.15 and 2.16 (8 s, 3H each, 8 OAc), 2.35 (bd, 1H, $J_{2',3'}$ 11.4 Hz, $J_{3',4'}$, $J_{3',Hb}$ 2.7 Hz H-3'), 2.60 (dd, 1H, $J_{3e,4}$ 4.4 Hz, H-3e), 2.92 (d, 1H, $J_{OH,Hb}$ 2.9 Hz, OH), 3.74 (s, 3H, CO$_2$CH$_3$), 3.77 (s, 3H, PhOCH$_3$), 3.88 (m, 1H, H-5'), 4.05 (m, 2H, $J_{6,7}$<1.5 Hz, H-5 and H-6), 4.10 (dd, 1H, $J_{8,9b}$ 5.4 Hz, $J_{9a,9b}$ 12.5 Hz, H-9b), 4.30 (dd, 1H, $J_{8,9a}$ 2.9 Hz, H-9a), 4.37–4.40 (m, 2H, H-6'a and H-6'b), 4.41 (bs, 1H, Hb), 4.83 (m, 1H, H-4), 4.88 (d, 1H, $J_{1',2'}$ 7.8 Hz, H-1'), 5.16 (bd, 1H, $J_{5,NH}$ 9.4 Hz, NH), 5.26 (d, 1H, H-4'), 5.33 (bd, 1H, $J_{7,8}$ 10.0 Hz, H-7), 5.39 (m, 1H), H-8), 5.43 (dd, 1H, H-2'), 6.80 and 7.10 (2 d, 2H each, PhOCH$_3$).

Example 4

Methyl 5-acetamido-4,7,8,9-tetra-O-acetyl-2,6-anhydro-3,5-dideoxy-2-C-{(R)-O-acetyl-[3-(p-methoxyphenyl 2,4,6-tri-O-acetyl-3-deoxy-β-D-galactopyranosidyl)]-methyl}-D-erythro-L-manno-nonate 21(S) and methyl 5-acetamnido-4,7,8,9-tetra-O-acetyl-2,6-anhydro-3,5-dideoxy-2-C-{(R)-hydroxy-[3-(p-methoxyphenyl 2,4,6-tri-O-acetyl-3-deoxy-β-D-galactopyranosidyl)]-methyl}-D-erythro-L-manno-nonate 20(S)

A solution of 19(S) (50 mg, 0.065 mmol) in anhydrous pyridine (5 mL) was reacted with $Ac_2O$ (0.1 mL) under nitrogen. After 48 hours at room temperature, the reaction mixture was quenched with $CH_3OH$ and evaporated under vacuum. The residue was dried by coevaporation with toluene and purified by chromatography on silica gel ($CHCl_3$—$CH_3OH$, v/v 45:1) to afford 21(S) and 20(S) as white solids in 38% (23 mg) and 61% (35 mg), respectively. 21(S); mp=127–130° C.; $[\alpha_D]^{22}=-1°$ (c 1, CHCl$_3$); $^1$H NMR (500 MHz, CDCl$_3$): δ1.74 (t, 1H, J$_{3a,4}$ 12.3 J$_{3a,3e}$ 12.7 Hz, H-3a), 1.78, 1.88, 2.01, 2.04, 2.07, 2.11, 2.14, 2.18 and 2.21 (9 s, 3H each, 9 OAc), 2.30 (dd, 1H, J$_{3e,4}$ 4.4 Hz, H-3e), 3.05 (m, 1H, J$_{2',3'}$ 11.4 Hz, J$_{3',Hb}$ 4.5 Hz, J$_{3',4'}$ 3.2 Hz, H-3'), 3.75 (s, 4H, H-5' and CO$_2$CH$_3$), 3.87 (s, 3H, PhOCH$_3$), 3.98 (dd, 1H, J$_{8,9b}$ 6.7 Hz, J$_{9a,9b}$ 12.3 Hz, H-9b), 3.89 (dd, 1H, J$_{5,6}$ 10.8 Hz, J$_{6,7}$ 2.4 Hz, H-6), 4.03–4.06 (m, 2H, H-6'a and H-6'b), 4.09 (dd, 1H, J$_{4,5}$ 10.5 Hz, J$_{5,NH}$ 10.0 Hz, H-5), 4.29 (dd, 1H, J$_{8,9a}$ 2.6 Hz, H-9a), 4.64 (d, 1H, H-4'), 4.78 (m, 1H, H-4), 5.08–5.13 (m, 3H, H-2', Hb and NH), 5.25 (d, 1H, J$_{1',2'}$ 7.6 Hz, H-1'), 5.31 (dd, 1H, J$_{7,8}$ 10.2 Hz, H-7), 5.78 (m, 1H, H-8), 6.80 and 7.00 (2 d, 2H each, PhOCH$_3$). Anal. Calcd for C$_{42}$H$_{55}$NO$_{23}$ (941.9): C 53.56, H 5.89; found C 53.54, H 5.81. 20(S). The purity of compound 20(S) was confirmed on TLC using both silica and aluminum oxide developed with chloroform:methanol (9:1); mp=132–134° C.; $[\alpha_D]^{22}=-9°$ (c 1, CHCl$_3$); $^1$H NMR (500 MHz, CDCl$_3$): δ1.80, 1.88, 2.03, 2.04, 2.10, 2.15, 2.18 and 2.20 (8 s, 3H each, 8 OAc), 2.30 (t, 1H, J$_{3a,4}$ 12.5 Hz, J$_{3a,3e}$ 13.2 Hz, H-3a), 2.40 (dd, 1H, J$_{3e,4}$ 4.7 Hz, H-3e), 2.49 (bd, 1H, J$_{OH,Hb}$ 5.2 Hz, OH), 2.82 (bd, 1H, J$_{2',3'}$ 11.4 Hz, J$_{3',Hb}$ 5.2 Hz, J$_{3',4'}$ 2.7 Hz, H-3'), 3.61 (m, 1H, H-5'), 3.76 (s, 3H, CO$_2$CH$_3$), 3.82 (s, 3H, PhOCH$_3$), 3.89 (dd, 1H, J$_{8,9b}$ 6.9 Hz, J$_{9a,9b}$ 12.4 Hz, H-9b), 3.97–4.08 (m, 5H, H-5, H-6, Hb, H-6'a and H-6'b), 4.30 (dd, 1H, J$_{8,9a}$ 2.6 Hz, H-9a), 4.60 (d, 1H, H-4'), 4.83 (m, 1H, H-4), 5.11 (bd, 1H, J$_{5,NH}$ 9.6 Hz, NH), 5.18 (d, 1H, J$_{1',2'}$ 7.7 Hz, H-1'), 5.27 (bd, 1H, J$_{6,7}$<1.9 Hz, J$_{7,8}$ 10.2 Hz, H-7), 5.44 (dd, 1H, H-2'), 5.68 (m, 1H, H-8), 6.80 and 7.00 (2 d, 2H each, PhOCH$_3$). HRMS: calcd for C$_{40}$H$_{53}$NO$_{22}$ [M=Na$^+$] 922.2942; found 922.2954. Anal. Calcd for C$_{40}$H$_{53}$NO$_{22}$ (899.9): C 53.39, H 6.11; found C 52.91, H 6.11.

Example 5

Methyl 5-acetamido-4,7,8,9-tetra-O-acetyl-2,6-anhydro-3,5-dideoxy-2-C-{(R)-O-acetyl-[3-(phenyl 2,4,6-tri-O-acetyl-3-deoxy-thio-β-D-galacto-pyranosidyl)]-methyl}-D-erythro-L-manno-nonate 22(S)

To a solution of 21(S) (27 mg, 0.029 mmol) in anhydrous toluene (3 mL) and under nitrogen were added thiophenol (15 μl, 0.143 mmol) and BF$_3$.OEt$_2$ (3.6 μl, 0.029 mmol). After 48 hours at 60° C., the reaction mixture was successively washed with satd. aq NaHCO$_3$ and H$_2$O, dried over anhydrous Na$_2$SO$_4$, filtered and the solvents were evaporated. The residue was purified by chromatography on silica gel (CHCl$_3$—CH$_3$OH, v/v 40:1) to afford 22(S) as a yellowish solid in 73% yield (19 mg). FABMS (+ve) [M+Na]$^+$ 950, [M+NH$_4$]$^+$ 945; $^1$H NMR (500 MHz, CDCl$_3$): δ~1.70 (ovl with OAc, H-3a), 1.79, 1.88, 2.01, 2.02, 2.07, 2.09, 2.10, 2.18 and 2.20 (9 S, 3H each, 9 OAc), 2.28 (dd, 1H, J$_{3e,4}$ 4.4 Hz, J$_{3a,3e}$ 12.8 Hz, H-3e), 3.05 (m, 1H, J$_{2',3'}$ 10.5 Hz, J$_{3',Hb}$ 4.7 Hz, J$_{3',4'}$ 2.9 Hz, H-3'), 3.76 (s, 4H, H-5' and CO$_2$CH$_3$), 3.93 (dd, 1H, J$_{8,9b}$ 6.1 HZ, J$_{9a,9b}$ 12.3 Hz, H-9b), 3.97 (dd, 1H, J$_{5,6}$ 10.2 Hz, J$_{6,7}$ 2.3 Hz, H-6), 4.03–4.06 (m, 2H, H-6'a and H-6'b), 4.07 (dd, 1H, J$_{4,5}$ 10.8 Hz, J$_{5,NH}$ 10.3 Hz, H-5), 4.29 (dd, 1H, J$_{8,9a}$ 2.6 Hz, H-9a), 4.66 (d, 1H, H-4'), 4.77 (m, 1H, H-4), 4.96 (dd, 1H, J$_{1',2'}$ 9.7 Hz, H-2'), 5.12 (bd, 1H, NH), 5.17 (d, 1H, H-1'), 5.32 (dd, 1H, J$_{7,8}$ 10.0 Hz, H-7), 5.75 (m, 1H, H-8), 7.40–7.50 (m, 5H, SPh).

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A compound of formula I:

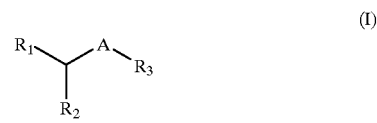

wherein:

R$_1$ is the residue of a sialic acid;

R$_2$ is hydrogen, hydroxy, or (C$_1$–C$_6$)alkanoyloxy;

R$_3$ is arylthio, optionally substituted on the aryl ring with 1, 2, 3, or 4 substituents independently selected from the group consisting of halo, nitro, cyano, trifluoromethoxy, (C$_1$–C$_6$)alkyl, (C$_1$–C$_6$)alkoxy, (C$_1$–C$_6$)alkanoyl, halo(C$_1$–C$_6$)alkyl, hydroxy(C$_1$–C$_6$)alkyl, (C$_1$–C$_6$)alkoxycarbonyl, (C$_1$–C$_6$)alkylthio, and (C$_1$–C$_6$)alkanoyloxy; and A is the residue of a monosaccharide.

2. The compound of claim 1 wherein R$_1$ is a residue of neuraminic acid, 3-deoxy-D-glycero-D-galacto-2-nonulosonic acid, or 3-deoxy-D-manno-2-octulosonic acid.

3. The compound of claim 1 wherein R$_1$ is methyl-5-acetamido-4,7,8,9-tetra-O-acetyl-3,5-dideoxy-D-glycero-α-D-galacto-non-2-ulopyranosyl)onate.

4. The compound of claim 1 wherein A is a glucose or galactose residue.

5. The compound of claim 1 wherein A is phenyl 2,4,6-tri-O-acetyl-3-eoxy-thio-β-D-galacto-pyranosid-3-yl.

6. The compound of claim 1 wherein R$_3$ is bonded to the anomeric carbon of A.

7. The compound of claim 1 wherein R$_3$ is phenylthio.

8. The compound of claim 1 which is methyl 5-acetamido-4,7,8,9-tetra-O-acetyl-2,6-anhydro-3,5-dideoxy-2-C-{(R)-O-acetyl-[3-(phenyl 2,4,6-tri-O-acetyl-3-deoxy-thio-β-D-galacto-pyranosidy]methyl}-D-erythro-L-manno-nonate.

9. A method for preparing a compound of formula 22a:

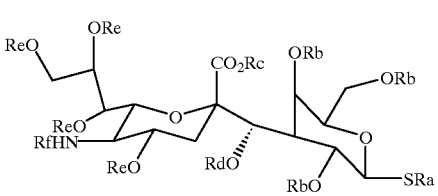

wherein:

Ra is aryl, optionally substituted with 1, 2, 3, or 4 substituents independently selected from the group consisting of halo, nitro, cyano, trifluoromethoxy, $(C_1-C_6)$alkyl, $(C_1-C_6)$alkoxy, $(C_1-C_6)$alkanoyl, halo$(C_1-C_6)$alkyl, hydroxy$(C_1-C_6)$alkyl, $(C_1-C_6)$alkoxycarbonyl, $(C_1-C_6)$alkylthio, and $(C_1-C_6)$alkanoyloxy;

each Rb is independently a suitable hydroxy protecting group;

Rc is $(C_1-C_6)$alkyl;

Rd is a suitable hydroxy protecting group;

each Re is independently a suitable hydroxy protecting group; and

Rf is $(C_1-C_6)$alkanoyl;

comprising reacting a corresponding compound of formula 21a:

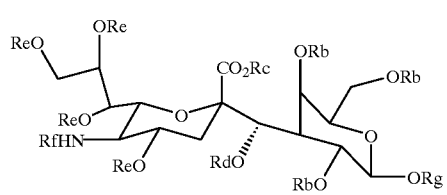

21a wherein Rg is aryl, optionally substituted with 1, 2, 3, or 4 substituents independently selected from the group consisting of $(C_1-C_6)$alkoxy;

with the requisite arylthiol, to provide the compound of formula 22a.

10. A compound of formula 22a:

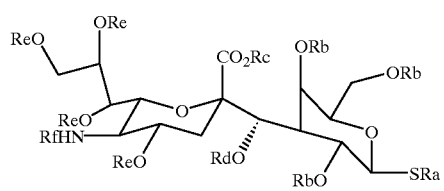

22a wherein:

Ra is aryl, optionally substituted with 1, 2, 3, or 4 substituents independently selected from the group consisting of halo, nitro, cyano, trifluoromethoxy, $(C_1-C_6)$alkyl, $(C_1-C_6)$alkoxy, $(C_1-C_6)$alkanoyl, halo$(C_1-C_6)$alkyl, hydroxy$(C_1-C_6)$alkyl, $(C_1-C_6)$alkoxycarbonyl, $(C_1-C_6)$alkylthio, and $(C_1-C_6)$alkanoyloxy;

each Rb is independently a suitable hydroxy protecting group;

Rc is $(C_1-C_6)$alkyl;

Rd is a suitable hydroxy protecting group;

each Re is independently a suitable hydroxy protecting group; and

Rf is $(C_1-C_6)$alkanoy.

11. A ganglioside that comprises a C-glycosyl component of formula II:

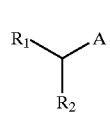

(II)

wherein:

$R_1$ is the residue of a sialic acid;

$R_2$ is hydrogen, hydroxy, or $(C_1-C_6)$alkanoyloxy; and

A is the residue of a monosaccharide.

12. The ganglioside of claim 11 wherein $R_1$ is a residue of neuraminic acid, 3-deoxy-D-glycero-D-galacto-2-nonulosonic acid, or 3-deoxy-D-manno-2-octulosonic acid.

13. The ganglioside of claim 11 wherein $R_1$ is methyl-5-acetamido-4,7,8,9-tetra-O-acetyl-3,5-dideoxy-D-glycero-α-D-galacto-non-2-ulopyranosyl)onate.

14. The ganglioside of claim 11 wherein A is a glucose or galactose residue.

15. The ganglioside of claim 11 wherein A is phenyl 2,4,6-tri-O-acetyl-3-deoxy-thio-β-D-galacto-pyranosid-3-yl.

16. The ganglioside of claim 11 which is:

Neu5Acα3GalCer;

Neu5Acα3Galβ4GlcCer;

GalNAcβ4(Neu5Acα3)Galβ4GlcCer;

Galβ3GalNAcβ4(Neu5Acα3)Galβ4GlcCer;

Neu5Acα3Galβ3GalNAcβ4Galβ4GlcCer;

Neu5Acα8Neu5Acα3Galβ4GlcCer;

GalNAcβ4(Neu5Acα8Neu5Acα3)Galβ4GlcCer;

Neu5Acα3Galβ3GalNAcβ4(Neu5Acα3)Galβ4GlcCer;

Galβ3GalNAcβ4(Neu5Acα8 Neu5Acα3)Galβ4GlcCer;

Neu5Acα8Neu5Acα3Galβ3GalNAcβ4(Neu5Acα3)Galβ4GlcCer;

Neu5Acα3Galβ3GalNAcβ4(Neu5Acα8Neu5Acα3)Galβ4GlcCer;

Galβ3GalNAcβ4(Neu5Acα8Neu5Acα8 Neu5Acα3)Galβ4GlcCer; or

Neu5Acα8Neu5Acα3Galβ3GalNAcβ4(Neu5Acα8-Neu5Acα3)Galβ4GlcCer.

17. A method for preparing a compound of formula 3a:

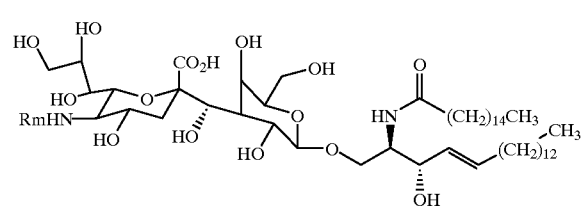

5a wherein $R_m$ is $(C_1-C_6)$alkanoyl; comprising hydrolyzing the ester of a corresponding compound of formula 28a:

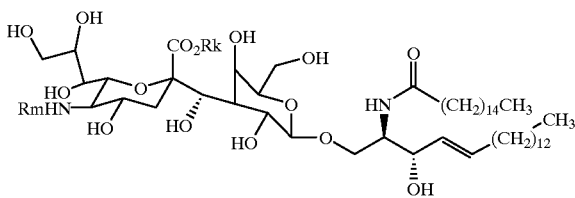

wherein $R_k$ is $(C_1–C_6)$alkyl, to provide the compound of formula 3a.

18. The method of claim 17 wherein $R_k$ is methyl; and $R_m$ is acetyl.

19. A method for preparing a compound of formula 4a:

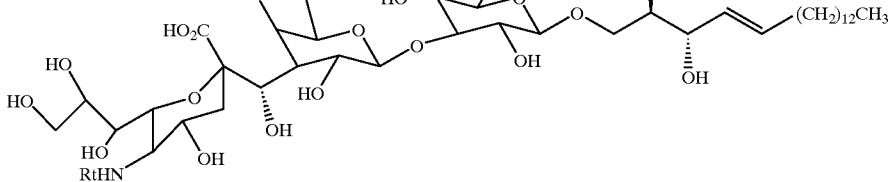

wherein $R_t$ is $(C_1–C_6)$alkanoyl, comprising hydrolyzing the ester of compound of formula 31a:

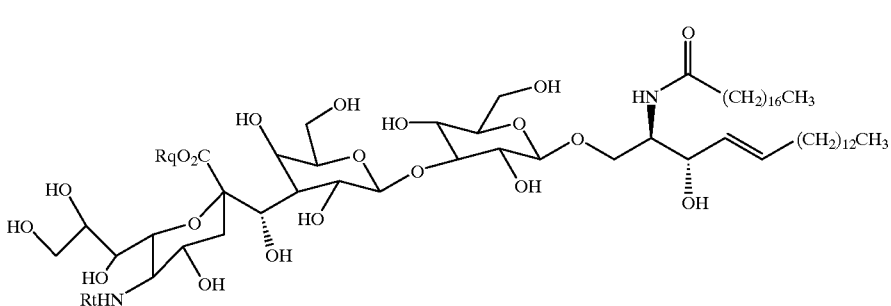

wherein $R_q$ is $(C_1–C_6)$alkyl, to provide the compound of formula 4a.

20. The method of claim 17 wherein $R_k$ is methyl; and $R_m$ is acetyl.

21. A method for preparing the C-glycoside of Neu5Acα3GalCer 3 comprising O-glycosylating a compound of formula 22 or an activated derivative thereof with ceramic acid, and deprotecting to provide 3.

22. A method for preparing Neu5Acα3Galβ4GlcCer 4 comprising O-glycosylating a compound of formula 22 or an activated derivative thereof with a suitably protected glucose, activating the anomeric position of the glucose, and O-glycosylating with ceramic acid to provide compound 4.

23. The ganglioside of claim 11 which is:

NeuAcα(2→3)Galβ(1→1')Cer,

NeuAcα(2→3) Galβ(1→4)Glcβ(1→1')Cer;

GalNAcβ(1→4)[Neu5Acα(2→3)]Galβ(1→4)Glc(1→1') Cer;

Galβ(1→3)GalNAcβ(1→4)[NeuAcα(2→3)]Galβ(1→4) Glc(1→1')Cer;

NeuAcα(2→3)Galβ(1→3)GalNAcβ(1→4)Galβ(1→4)Glc (1→1')Cer; or

NeuAcα(2→8)NeuAcα(2→3)Galβ(1→4)Glc(1→1')Cer. (1→4)Glc(1→1')Cer;

24. The ganglioside of claim 11 which is:
GalNAcβ(1→4)[NeuAcα(2→8)NeuAcα(2→3)]Galβ

NeuAcα(2→3)Galβ(1→3)GalNAcβ(1→4)[Neu Acα (2→3)]Galβ(1→4)Glc(1→1')Cer;

Galβ(1→3)GalNAcβ(1→4)[NeuAcα(2→8)NeuAca (2→3)]Galβ(1→4)Glc(1→1')Cer;

NeuAcα(2→8)NeuAcα(2→3)Galβ(1→3)GalNAcβ(1→4) [NeuAcα(2→3)]Galβ(1→4) Glc(1→1')Cer;

NeuAcα(2→3)Galβ(1→3)GalNAcβ(1→4)[NeuAcα(2→8) NeuAcα(2→3)]Galβ(1→4) Glc(1→1')Cer;

Galβ(1→3)GalNAcβ(1→4)[NeuAcα(2→8)NeuAcα(2→8) NeuAcα(2→3)]Galβ(1→4) Glc(1→1')Cer; or

NeuAcα(2→8)NeuAcα(2→3)Galβ(1→3)GalNAcβ(1→4) [NeuAcα(2→8)NeuAcα(2→3)]Galβ(1→4) Glc(1→1') Cer.

* * * * *

UNITED STATES PATENT AND TRADEMARK OFFICE
CERTIFICATE OF CORRECTION

PATENT NO. : 6,245,902 B1
DATED : June 12, 2001
INVENTOR(S) : Linhardt et al.

It is certified that error appears in the above-identified patent and that said Letters Patent is hereby corrected as shown below:

Column 1,
Line 11, delete "atta, S. G." and insert -- Matta, S. G. --, therefor.

Column 2,
Line 6, delete "N-acetylneuraninic" and insert -- N-acetylneuraminic --, therefor.

Column 4,
Line 17, delete "formula22a" and insert -- formula 22a --, therefor.
Line 35, delete "and $C_1$-$C_6$)" and insert -- and ($C_1$-$C_6$) --, therefor.

Column 10,
Line 6, delete "2,4,6trio-O" and insert -- 2,4,6-trio-O --, therefor.

Column 13,
Line 14, delete "RfHN" and insert -- RtHN --, therefor.
Line 27, delete "RfHN" and insert -- RtHN --, therefor.

Column 20,
Line 1, delete "omithine and insert -- ornithine --, therefor.

Column 21,
Line 34, delete "acetamaido" and insert -- acetamido --, therefor.

Column 23,
Line 18, delete "afforded 91% as" and insert -- afforded 9 as --, therefor.

Column 24,
Line 30, delete "ThF" and insert -- THF --, therefor.
Line 67, delete "warm" and insert -- warm --, therefor.

Column 25,
Line 38, delete "acetaniido" and insert -- acetamido --, therefor.
Line 43, delete "18(R)-96818(S)" and insert -- 18(R)-18(S) --, therefor.
Line 53, delete "=+4" and insert -- =+4° --, therefor.

Column 26,
Line 19, delete "acetanido" and insert -- acetamido --, therefor.
Line 46, delete "1H)," and insert -- 1H, --, therefor.
Line 55, delete "acetamnido" and insert -- acetamido --, therefor.

UNITED STATES PATENT AND TRADEMARK OFFICE
CERTIFICATE OF CORRECTION

PATENT NO. : 6,245,902 B1
DATED : June 12, 2001
INVENTOR(S) : Linhardt et al.

It is certified that error appears in the above-identified patent and that said Letters Patent is hereby corrected as shown below:

Column 28, claim 5,
Line 45, delete "3-eoxy" and insert -- 3-deoxy --, therefor.

Column 29, claim 10,
Line 65, delete "alkanoy" and insert -- alkanoyl --, therefor.

Column 32, claim 23,
Line 7, delete "Cer," and insert -- Cer; --, therefor.
Line 17, delete "(1→4)Glc(1→1')Cer;".

Column 32, claim 24,
Line 35, after "Galβ" insert -- (1→4)Glc(1→1')Cer; --, therefor.

Signed and Sealed this

Twenty-second Day of January, 2002

Attest:

JAMES E. ROGAN
*Attesting Officer*    *Director of the United States Patent and Trademark Office*